US007125658B2

(12) United States Patent
Rothstein et al.

(10) Patent No.: US 7,125,658 B2
(45) Date of Patent: Oct. 24, 2006

(54) SMALL PROTEIN THAT INTERACTS WITH A RIBONUCLEOTIDE REDUCTASE SUBUNIT AND USES THEREOF

(75) Inventors: Rodney Rothstein, Maplewood, NJ (US); Xiaolan Zhao, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 661 days.

(21) Appl. No.: 09/814,661

(22) Filed: Mar. 22, 2001

(65) Prior Publication Data

US 2002/0151016 A1    Oct. 17, 2002

Related U.S. Application Data

(63) Continuation of application No. PCT/US99/22260, filed on Sep. 24, 1999, which is a continuation-in-part of application No. 09/159,858, filed on Sep. 24, 1998, now abandoned.

(51) Int. Cl.

| *C12Q 1/00* | (2006.01) |
| *C12Q 3/00* | (2006.01) |
| *C12N 1/04* | (2006.01) |
| *C12N 5/00* | (2006.01) |
| *G01N 33/48* | (2006.01) |

(52) U.S. Cl. ............................... 435/3; 435/4; 435/375; 435/384; 435/260; 436/63

(58) Field of Classification Search .................... 435/4, 435/3, 260, 375, 384; 436/63

See application file for complete search history.

(56) References Cited

U.S. PATENT DOCUMENTS

| 4,393,041 A | * | 7/1983 | Brown et al. ................. 424/426 |
| 4,889,806 A | | 12/1989 | Olsen et al. |
| 5,767,134 A | * | 6/1998 | Li et al. ....................... 514/353 |
| 5,834,279 A | | 11/1998 | Rubin et al. |
| 6,030,942 A | * | 2/2000 | Cooperman et al. ............ 514/9 |

FOREIGN PATENT DOCUMENTS

| EP | 0726 277 A2 | 8/1996 |
| WO | WO 00/17225 A3 | 3/2000 |

OTHER PUBLICATIONS

Nasr et al (C R Acad Sci III, 1994, vol. 317, pp. 607-613), abstract.*
Sanchez et al (Science, 1996, vol. 271, pp. 357-360).*
Abstract of Theisinger et al, Human Genetics, 1992, vol. 89, pp. 681-682).*
Zhao et al, Molecular Cell, 1998, vol. 2, pp. 329-340).*
Cohen et al, Nature, 1986, vol. 321, pp. 441-443.*
Dutia et al, Nature, 1986, vol. 321, pp. 439-441.*
U.S. Appl. No. 09/159,858, filed Sep. 24, 1998, on behalf of Rodney Rothstein et al.
International Search Report issued on May 3, 2000 in connection with PCT International Application No. PCT/US99/22260, filed Sep. 24, 1999, International Publication No. WO 00/17225 A3, published Mar. 30, 2000, on behalf of The Trustees of Columbia University In The City Of New York.
Written Opinion issued Sep. 12, 2000 in connection with PCT International Application No. PCT/US99/22260, filed Sep. 24, 1999, International Publication No. WO 00/17225 A3, published Mar. 30, 2000, on behalf of The Trustees of Columbia University In The City Of New York.
International Preliminary Examination Report issued on Jan. 11, 2001 in connection with PCT International Application No. PCT/US99/22260, filed Sep. 24, 1999, International Publication No. WO 00/17225 A3, published Mar. 30, 2000, on behalf of The Trustees of Columbia University In The City Of New York.
Arap, W. et al. (1998) "Cancer Treatment by Targeted Drug Delivery to Tumor Vasculature in a Mouse Model," *Science* 279: 377-380.
Allen, J.B. et al. (1994) "The SAD1/RAD53 protein kinase controls multiple checkpoints and DNA damage-induced transcription in yeast," *Genes Dev.* 8: 2401-2415.
Barlow, C. et al. (1996) "*Atm*-Deficient Mice: A Paradigm Of Ataxia Telangiectasia," *Cell* 86: 159-171.
Desany, B.A. et al. (1998) "Recovery from DNA replicational stress Is the essential function of the S-phase checkpoint pathway," *Genes Dev.* 12: 2956-70.
Elledge, S.J. (1996) "Cell cycle checkpoints: preventing an identity crisis," *Science* 274: 1664-1672.
Elson, A. et al. (1996) "Pleiotropic defects in ataxia-telangiectasia protein-deficient mice," *Proc. Natl. Acad. Sci. USA* 93: 13084-13089.

(Continued)

Primary Examiner—Karen A. Canella
(74) *Attorney, Agent, or Firm*—John P. White, Esq.; Cooper & Dunham LLP

(57) ABSTRACT

The present invention provides for an isolated Sml1 protein or a homologue thereof. The present invention also provides for a screening assay for identifying compounds that are capable of reducing the division rate of a cell by altering an interaction between a ribonucleotide reductase and a Sml1 protein in the cell, which comprises: (a) contacting the cell with a compound, (b) comparing the division rate of the cell in step (a) with the division rate of the cell in the absence of the compound so as to determine whether the compound alters the interaction between the ribonucleotide reductase and the Sml1 protein of the cell, thereby reducing the cell division rate of the cell.

4 Claims, 21 Drawing Sheets

OTHER PUBLICATIONS

Fay, D.S. et al. (1997) "Mutations in *SPK1/RAD53* that specifically abolish checkpoint but not growth-related functions," *Curr. Genet.* 31: 97-105.

James, P. et al. (1996) "Genomic libraries and a host strain designed for highly efficient two-hybrid selection in yeast," *Genetics* 144: 1425-1436.

Kato, R. et al. (1994) "An essential gene, *ESR1*, is required for mitotic cell growth, DNA repair and meiotic recombination in *Saccharomyces cerevisiae*," *Nucleic Acids Res.* 22: 3104-3112.

Koch, C. et al. (1993) "A role for the transcription factors Mbpl and Swi4 in progression from G1 to S phase," *Science* 261: 1551-1557.

Lecrenier, N. et al. (1995) "Overexpression of the *RNR1* gene rescues *Saccharomyces cerevisiae* mutants in the mitochondrial DNA polymerase-encoding *MIP1* gene," *Mol. Gen. Genet.* 249: 1-7.

Liuzzi, M. et al. (1994) "A potent peptidomimetic inhibitor of HSV ribonucleotide reductase with antiviral activity *in vivo*," *Nature* 372: 695-698.

Reichard, P. (1988) "Interactions between deoxyribonucleotide and DNA synthesis," *Ann. Rev. Biochem.* 57: 349-374.

Sanchez, Y. et al. (1996) "Regulation of *RAD53* by the *ATM*-like kinases *MEC1* and *TEL1* in yeast cell cycle checkpoint pathways," *Science* 271: 357-360.

Shewach, D.S. et al. (1996) "Gemcitabine and radiosensitization in human tumor cells," *Invest. New Drugs* 14: 257-263.

Shiloh, Y. (1997) "Ataxia-telangiectasia and the Nijmegen breakage syndrome: related disorders but genes apart," *Annu. Rev. Genet.* 31: 635-662.

Sun, Z. et al. (1996) "Spkl/Rad53 is regulated by Mecl-dependent protein phosphorylation in DNA replication and damage checkpoint pathways," *Genes Dev.* 10: 395-406.

Szekeres, T. et al. (1994) "Biochemical and antitumor activity of trimidox, a new inhibitor of ribonucleotide reductase," *Cancer Chemther. Pharmacol.* 34: 63-66.

Vallen, E.A. et al. (1999) "Interaction between the *MEC1*-dependent DNA synthesis checkpoint and G1 cyclin function in *Saccharomyces cerevisiae*," *Genetics* 151: 459-71.

Wang, Y.A. et al. (1997) "Loss of *p21* increases sensitivity to ionizing radiation and delays the onset of lymphoma in *atm*-deficient mice," *Proc. Natl. Acad. Sci. USA* 94: 14590-14595.

Westphal, C.H. et al. (1997) "Genetic interactions between atm and *p53* influence cellular proliferation and irradiation-induced cell cycle checkpoints," *Cancer Res.* 57: 1664-1667.

Xu, Y. et al. (1996) "Targeted disruption of *ATM* leads to growth retardation, chromosomal fragmentation during meiosis, immune defects, and thymic lymphoma," *Genes Dev.* 10:2411-2422.

Xu, Y. et al. (1996) "Dual roles of *ATM* in the cellular response to radiation and in cell growth control," *Genes Dev.* 10: 2401-2410.

Zakian, V.A. (1995) "*ATM*-related genes: what do they tell us about functions of the human gene?," *Cell* 82: 685-687.

Zheng, P. et al. (1993) "*SPK1* is an essential S-phase-specific gene of *Saccharomyces cerevisiae* that encodes a nuclear serine/threonine/tyrosine kinase," *Mol. Cell. Biol.* 13: 5829-5842.

Barrell et al. (1997) (Genbank Accession No. Z46729, National Center for Biotechnology Information, National Library of Medicine, Bethesda, Maryland).

Lewin (1988) "When Does Homology Mean Something Else?" *Science* 237: 1570.

Miyakawa et al. (1991) Genbank Accession No. X54964 (National Center for Biotechnology Information, National Library of Medicine; Bethesda, Maryland).

Reeck et al. (1987) "Homology In Proteins and Nucleic Acids: A Terminology Muddle and a Way Out of It," *Cell* 50: 667.

Sambrook et al. (1987) *Molecular Cloning, a Laboratory Manual* (Cold Spring Harbor Press) : 16.3-16.4.

Devlin et al. (1997) Genbank Accession No. Q04964, Hypothetical 11.8 kD protein in OGG1-CNA2 intergenic region, Gene Sequence.

Ahn et al. (1993) "The Structural and Functional Diversity of Dystrophin," *Nature Genetics* 3: 283-291.

Cawthon et al. (1991) "cDNA Sequence and Genomic Structure of EVI2B, a Gene Lying Within An Intro of the Neurofibromatosis Type 1 Gene," *Genomics* 9: 446-460.

Harris et al. (1995) "Polycystic Kidney Disease 1: Identification and Analysis of the Primary Defect," *J. Am. Soc. Nephrology* 6: 1125-1133.

Liu et al. (1991) *Mol. Gen. Genet.* 227: 52-59.

Reiger et al. (1976) *Glossary of Genetics and Cytogenetics, Classical and Molecular*, 4th Edition (Springer-Verlag, Berlin) pp. 17-18.

Saitoh et al. (1991) *Biomed. Res.* 12: 215-218.

Bradford, M.M. (1976) "A Rapid and Sensitive Method For The Quantitation of Microgram Quantities of Protein Utilizing the Principle of Protein-Dye Binding," *Anal. Biochem.* 72: 248-254.

Chance, B. and Herbert, D. (1950) "The Enzyme-substrate Compounds of Bacterial Catalase and Peroxides," *J. Biochem.* 46: 402-414.

Davis, R. et al. (1994) "Purification, Characterization and Localization of Subunit Interaction Area of Recombinant Mouse Ribonucleotide Reductase R1 Subunit," *J. Biol. Chem.* 269: 23171-23176.

Elledge, S.J. and Davis, R.W. (1987) "Identification And Isolation of the Gene Encoding the Small Subunit of Ribonucleotide Reductase from *Saccharomyces cerevisiae*: DNA Damage-Inducible Gene Required for Mitotic Viability," *Mol. Cell Biol.* 7: 2783-2793.

Elledge, S.J. and Davis, R.W. (1990) "Two Genes Differentially Regulated in the Cell Cycle and By DNA-damaging Agents Encode Alternative Regulatory Subunits Of Ribonucleotide Reductase," *Genes Dev.* 4: 740-751.

Engetröm, Y. et al. (1979) "Ribonucleotide Reductase from Calf Thymus. Purification and Properties," *Biochemistry* 18: 2941-2948.

Huang, M. and Elledge, S.J. (1997) "Identification of *RNR4*, Encoding a Second Essential Small Subunit of Ribonucleotide Reductase in *Saccharomyces cerevisiae*," *Mol. Cell. Biol.* 17: 6105-6113.

Hurd, H.K. et al. (1987) "Identification of the Gene for the Yeast Ribonucleotide Reductase Small Subunit and Its Inducibility by Methyl Methanesulfonate," *Mol. Cell. Biol.* 7: 3673-3677.

Ingemarson, R. and Thelander, L. (1996) "A Kinetic Study on the Influence of Nucleoside Triphosphate Effectors on Subunit Interaction in Mouse Ribonucleotide Reductase," *Biochemistry* 35: 8603-8609.

Jönsson, U. et al. (1991) "Real-Time Biospecific Interaction Analysis Using Surface Plasmon Resonance and a Sensor Chip Technology," *BioTechniques* 11: 620-627.

Lycksell, P. -O. et al. (1994) "$^1$H NMR Studies of Mouse Ribonucleotide Reductase: The R2 Protein Carboxyl-Terminal Tail, Essential for Subunit Interaction, Is Highly Flexible But Becomes Rigid in the Presence of Protein R1," *Biochemistry* 33: 2838-2842.

Mann, G.J. et al. (1991) "Purification and Characterization of Recombinant Mouse and Herpes Simplex Virus Ribonucleotide Reductase R2 Subunit," *Biochemistry* 30: 1939-1947.

Reichard, P. (1993) "From RNA to DNA, Why So Many Ribonucleotide Reductases?" *Science* 260: 1773-1777.

Rova, U. et al. (1995) "Evidence by Site-Directed Mutagenesis Supports Long-Range Electron Transfer in Mouse Ribonucleotide Reductase," *Biochemistry* 34: 4267-4275.

Studier, F.W. et al. (1990) "Use of T7 RNA Polymerase to Direct Expression of Cloned Genes," *Methods Enzymol.* 185: 60-89.

Thelander, L. et al. (1980) "Ribonucleotide Reductase from the Calf Thymus: Separation of the Enzyme into Two Nonidentical Subunits, Proteins M1 and M2," *J. Biol. Chem.* 255: 7426-7432.

Thelander, L. and Gräslund, A. (1994) "Ribonucleotide Reductase in Mammalian Systems," *Metal Ions In Biological Systems* (Marcel Dekker; New York) : 109-129.

Wang, P.J. et al. (1997) "Rnr4p, a Novel Ribonucleotide Reductase Small-Subunit Protein," *Mol. Cell. Biol.* 17: 6114-6121.

Weinert, T. (1998) "DNA Damage and Checkpoint Pathways: Molecular Anatomy and Interactions with Repair," *Cell* 94: 555-558; and.

Zhao, X. et al. (1998) "A Suppressor of Two Essential Checkpoint Genes Identifies a Novel Protein that Negatively Affects dNTP Pools," *Mol. Cell* 2: 329-340.

* cited by examiner

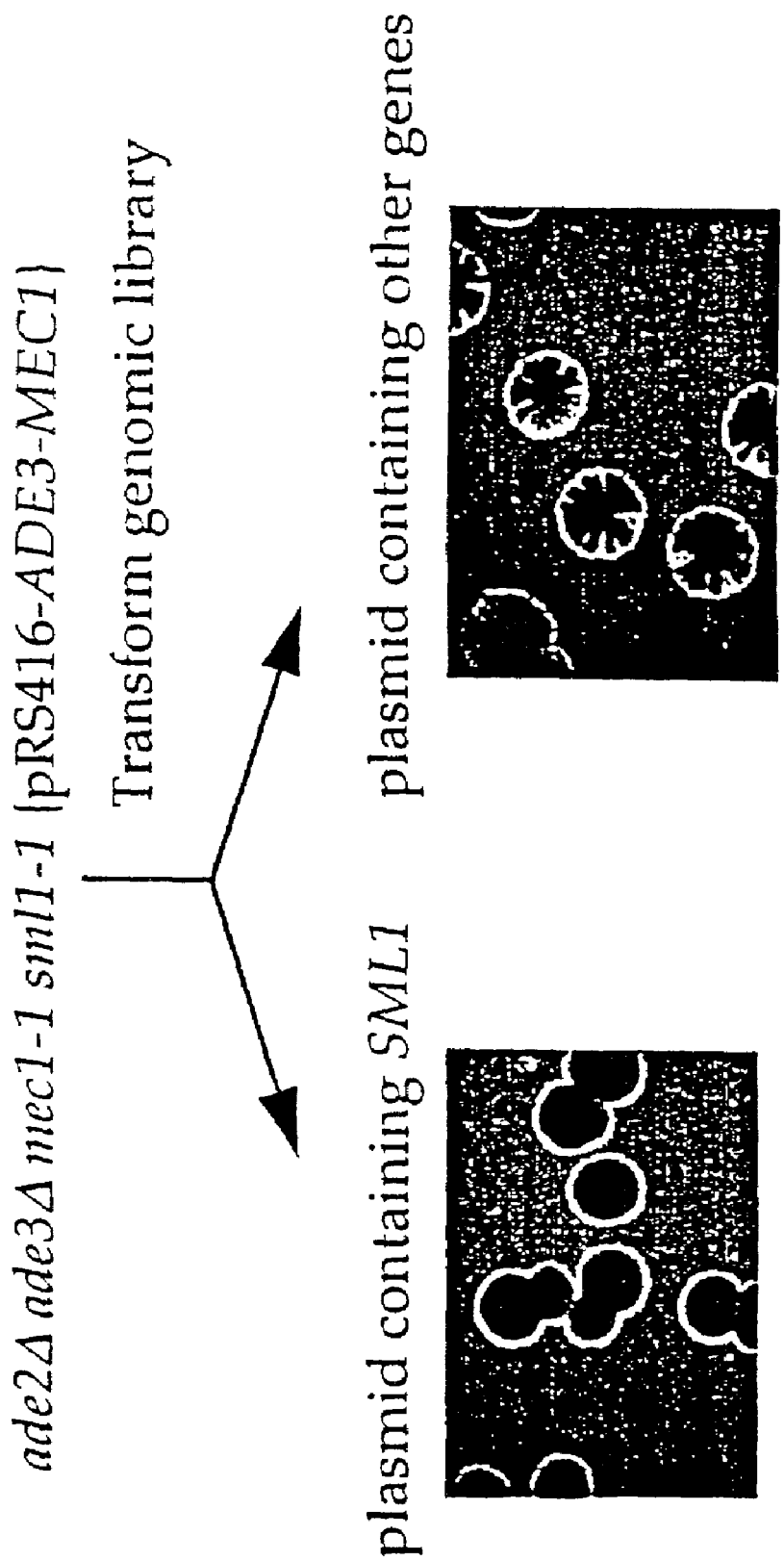

FIG. 1C

```
AATGAGCAACCGTGTCAACAAGAGTGTCAAGACCGGCTACTTATTCCCCAAGGATCACGTTCCTTCTGCCAACATCATTG
CCGTCGAACGTCGGCGGGTCTCTTCTGACATTGGTAAGAATACTTCCAACTAAGAGACATGCTTCTCTTTTTTTT
GTAGGCCAATGATAGGAAAGAACAATAGATTATAAATACGTCAGAATATAGTAGATGTTTTATGTTTAGACCTCGTA
CATAGGAATAATTGACGTTTTTTTGGCCAACATTGAATTTTTTTGTTACCTCGCGCTGAGCCAAACGGGCTCC
ACTACCCGCCGGTCGCCATTTGGAAGTCATCCGTCCAAAAGGAAATAGCCATAACATATCGTTACTGTTTTTGGA
ACATCGCCCCGTTTCGCCCGATTCCGCCTCAGCGGGTATAAAAGAGATCTTTTTTTTCCGGCTGTCCCTTC
CATTTTAAATGCTTATCTGCTCCTTTGTGATCTTACGGTCTCACTAACCTCTCTCAACTGCTCAATAATTCCCGCT
```

|     | ATG | CAA | AAT | TCC | CAA | GAC | TAC | TTT | TAC | GCT | CAA | AAT | CGC | TGC | CAA | CAA | CAA | GCC | CCT |
| --- | --- | --- | --- | --- | --- | --- | --- | --- | --- | --- | --- | --- | --- | --- | --- | --- | --- | --- | --- |
| 1   | M   | Q   | N   | S   | Q   | D   | Y   | F   | Y   | A   | Q   | N   | R   | C   | Q   | Q   | Q   | A   | P   |
|     | TCC | ACA | TTG | CGT | ACC | GTG | ACC | ATG | GCG | GAA | TTT | AGA | AGG | GTG | CCT | TTG | CCA | CCT | ATG | GCT |
| 21  | S   | T   | L   | R   | T   | V   | T   | M   | A   | E   | F   | R   | R   | V   | P   | L   | P   | P   | M   | A   |
|     | GAG | GTT | CCT | ATG | TTG | TCT | ACT | CAA | AAC | TCC | ATG | GGC | AGC | TCC | GCC | TCT | GCC | TCT | TCT |
| 41  | E   | V   | P   | M   | L   | S   | T   | Q   | N   | S   | M   | G   | S   | S   | A   | S   | A   | S   | S   |
|     | TCA | TTA | GAA | ATG | TGG | GAA | AAG | GAT | TTG | GAG | GAG | AGA | CTC | AAC | TCT | ATC | GAT | CAT | GAC | ATG |
| 61  | S   | L   | E   | M   | W   | E   | K   | D   | L   | E   | E   | R   | L   | N   | S   | I   | D   | H   | D   | M   |
|     | AAC | AAC | AAC | AAA | TTT | GGT | TCT | GGC | GAA | CTA | AAA | TCT | ATG | TTC | AAC | CAG | GGT | AAG | GTC | GAG |
| 81  | N   | N   | N   | K   | F   | G   | S   | G   | E   | L   | K   | S   | M   | F   | N   | Q   | G   | K   | V   | E   |
|     | GAA | ATG | GAC | TTC | TAA | AGTTCCTTTCATACTCTTCTTTCTCATTCCCACTAGTCTGTCTTTTC |
| 101 | E   | M   | D   | F   | *   | |

```
TTCTCTTAGATACCCTTCTTTTCAGGACTCGTCCTACTATTGTGTCATTCTGAAACATCTCCCGTGCATTT
TCCTTTCCCTTTATACATATATATATATATATATATATGTCTTCTACGTATTTTGTATTTCTGTGTCTTTAT
CAAAGATAGTCTATAATACGTTTGATACAGCTAGCGCCAACATTGTCCCCTCTCTGATCAATGCTTT
```

*mrc1Δ/+ sml1Δ/+*

*mrc1Δ/+ sml1Δ/+ dun1Δ/+*

*mrc1Δ/+ sml1Δ/+ tel1Δ/+*

*rad53Δ/+ sml1Δ/+*

*sml1Δ*

*SML1*

*2XSML1*

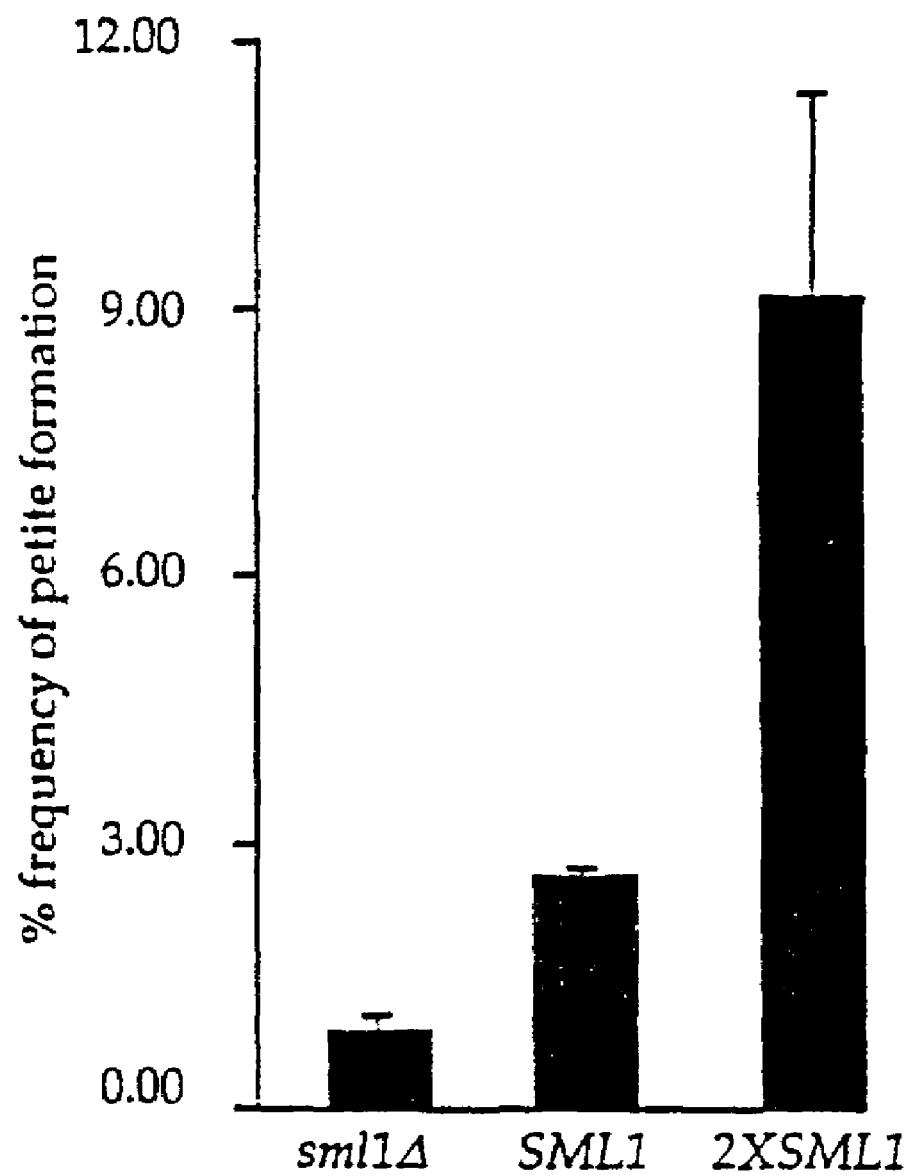

*mip1-1*
*sml1Δ mip1-1*
*MIP1*

YPGlycerol
at 37°C

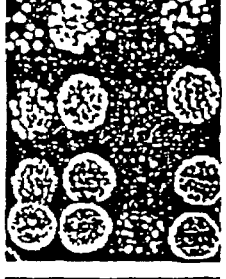
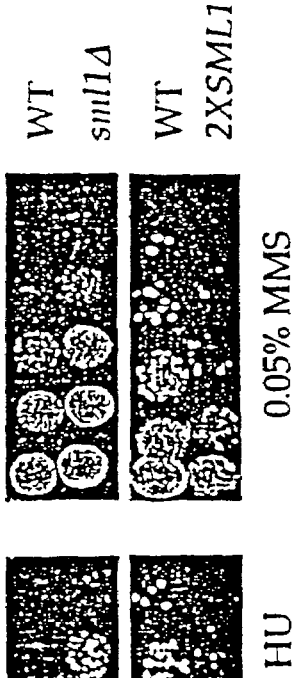
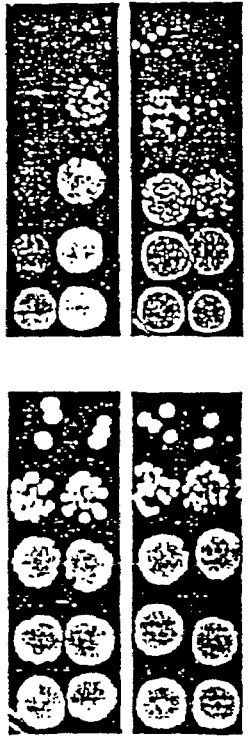
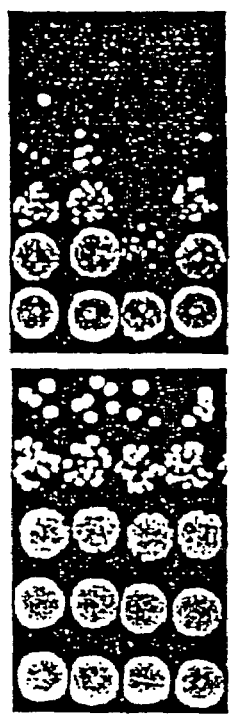

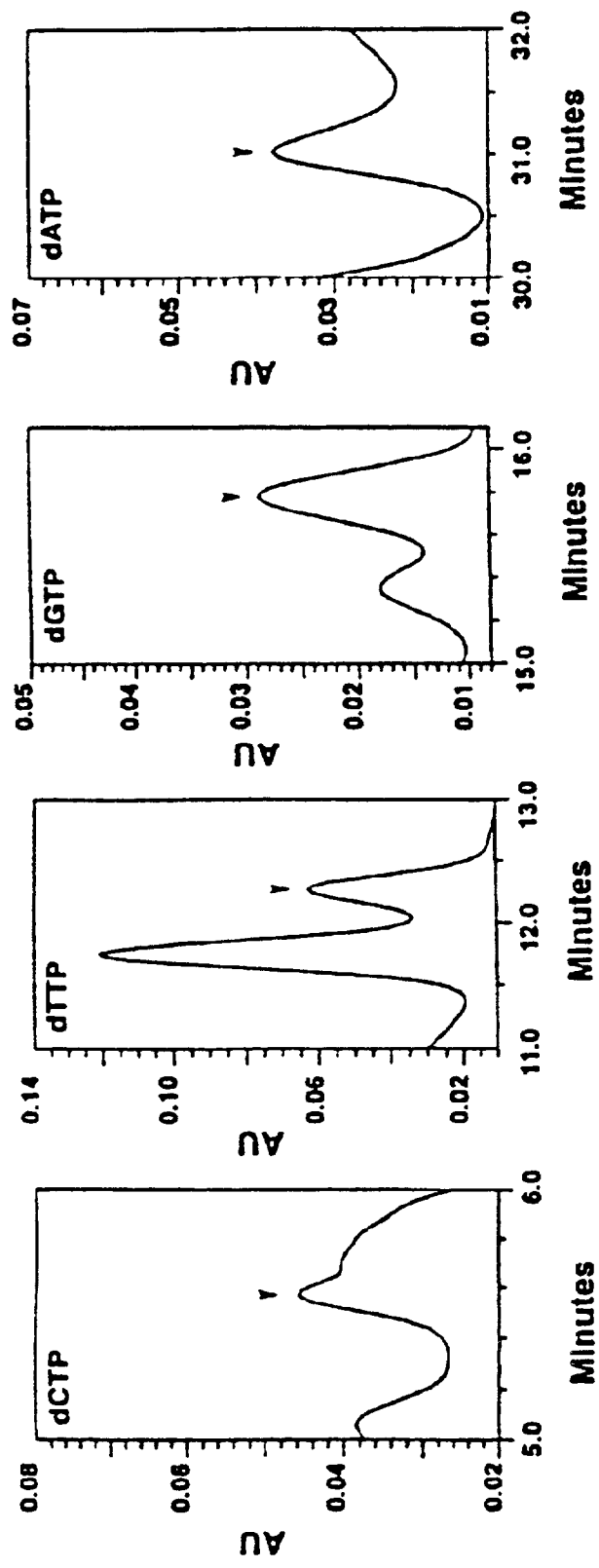
FIG. 5A Wild-type — dCTP
FIG. 5B dTTP
FIG. 5C dGTP
FIG. 5D dATP

*sml1Δ*

FIG. 5I

|  | dCTP | dTTP | dGTP | dATP |
|---|---|---|---|---|
| wild-type | 386 | 869 | 171 | 327 |
| sml1Δ | 1071 | 2118 | 414 | 855 |
| fold increase | 2.6 | 2.4 | 2.4 | 2.6 |

Deoxyribonucleotide levels are shown as pmol/$10^9$ cells

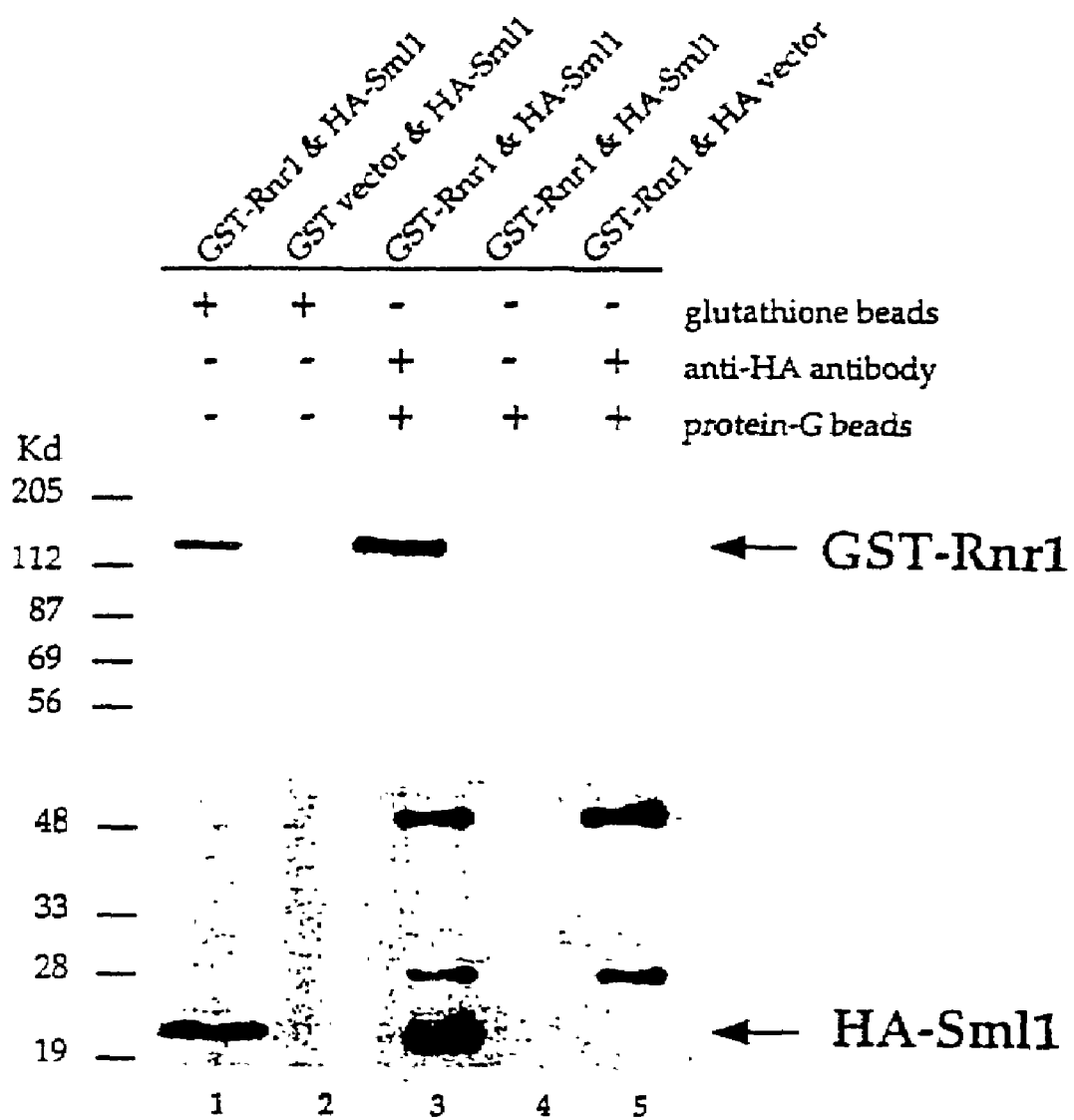

SMALL PROTEIN THAT INTERACTS WITH A RIBONUCLEOTIDE REDUCTASE SUBUNIT AND USES THEREOF

This application is a continuation of PCT International Application No. PCT/US99/22260, filed 24 Sep. 1999, designating the United States of America, which is a continuation-in-part and claims priority of U.S. Ser. No. 09/158,858, filed Sep. 24, 1998, now abandoned, the contents of which are hereby incorporated by reference into the present application.

The invention disclosed herein was made with Government support under Grant No. NIH GM50237 from the Department of Health and Human Services (National Institutute of Health). Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

In the yeast *Saccharomyces cerevisiae,* the Mec1 and Rad53 proteins are involved in the G1, S and G2 cell cycle checkpoint pathways (reviewed by Elledge, 1996). In the presence of DNA damage or a DNA replication block(s), these proteins are required to arrest or slow cell cycle progression. At the same time, they induce transcription of the genes encoding ribonucleotide reductase (RNR), which catalyzes the rate-limiting step in dNTP synthesis that is necessary for replication and repair (reviewed by Reichard, 1988). In addition to their involvement in checkpoint pathways, Mec1 and Rad53 are both essential for cell growth (Zheng et al., 1993; Kato and Ogawa, 1994). This property distinguishes them from most other checkpoint genes, which are dispensable for growth.

Two observations suggest that Rad53 acts after Mec1 for both checkpoint and essential functions. First, the phosphorylation of Rad53 in response to DNA damage is absent in a mec1 mutant (Sanchez et al., 1996; Sun et al., 1996). Second, overproduction of Rad53 suppresses mec1 lethality and partially suppresses its hydroxyurea sensitivity (Sanchez et al., 1996). Since both proteins function as signal transducers in a common checkpoint pathway, they may play a similar role in the regulation of mitotic cell growth. However, the exact nature of their essential functions is not known and whether their checkpoint and cell growth functions overlap is still an open question.

Mec1 is a member of the PI3-kinase family, composed of proteins that have PI kinase or protein kinase activity (reviewed by Zakian, 1995; Shiloh, 1997). Interestingly, ATM and Atm, homologs of Mec1 in human and mice respectively, also play dual roles in cell growth and cell cycle checkpoint function (reviewed by Friedberg, 1995; Shiloh, 1997). Mutations in the ATM gene result in a recessive autosomal disease, ataxia telangiectasia (AT), a multi-system disorder associated with a high risk of cancer. Mitotic cells from AT patients grow poorly, senesce prematurely and exhibit a higher nutrient requirement in vitro. In addition, these cells are checkpoint deficient since they are sensitive to ionizing radiation and display radioresistant DNA synthesis. The phenotype of Atm-deficient mice mimics that of AT patients, and fibroblasts from these mice exhibit growth defects and radioresistant DNA synthesis similar to that observed in AT cells (Barlow et al., 1996; Xu et al., 1996; Xu and Baltimore, 1996; Elson et al., 1996). The growth defect of the Atm-deficient cells correlates with a failure to enter S phase efficiently and can be suppressed by deletion of either the p53 or p21 gene (Xu and Baltimore, 1996; Westphal et al., 1997; Wang et al., 1997b). The molecular basis for the cell growth functions of ATM and Atm is not clear. Given the conservation between Mec1 and these two proteins, an investigation of the role of Mec1 in mitotic growth may shed light on the cell growth functions of ATM and Atm.

SUMMARY OF THE INVENTION

The present invention provides for an isolated Sml1 protein or a homologue thereof. The present invention also provides for a screening assay for identifying compounds that are capable of reducing the division rate of a cell by altering an interaction between a ribonucleotide reductase and a Sml1 protein in the cell, which comprises: (a) contacting the cell with a compound, (b) comparing the division rate of the cell in step (a) with the division rate of the cell in the absence of the compound so as to determine whether the compound alters the interaction between the ribonucleotide reductase and the Sml1 protein of the cell, thereby reducing the cell division rate of the cell. The present invention also provides for a method for treating cancer in a cancer patient which comprises adminstering to the patient an amount of a compound effective to increase an interaction between a ribonucleotide reductase protein and an Sml1protein in cancer cells of the patient, thereby reducing cell division rate of the cancer cells in the patient and treating the cancer.

BRIEF DESCRIPTION OF THE FIGURES

FIGS. 1A–1C. Cloning the SML1 gene (FIG. 1A) Outline of the cloning strategy. DNA from a CEN-LEU2 plasmid-based genomic library was transformed into the indicator strain, U940. Transformants were plated on medium lacking leucine and SML1-containing plasmids were identified as solid red transformants (See Experimental Details).

(FIG. 1B) The genes and ORFs on the insert of pWJ739 are shown with arrows indicating the direction of transcription. Three deletion constructs and their ability to complement sml1 are shown. Restriction sites: H, HindIII; N, NcoI; P, PmlI; S, SacII; Sn, SnaBI.

(FIG. 1C) DNA sequence of the SML1 region (SEQ ID NO: 1) is shown with the predicted amino acid sequence of the SML1 ORF (SEQ ID NO: 2). Two 11 base pair direct repeats are underlined. The putative TATA box is indicated by large bold letters.

FIGS. 3A–3D. SML1 affects mitochondrial propagation (FIGS. 3A–C) Cells were streaked on YPD medium and incubated at 30° C. for 5 days. In the W303 genetic background, petite cells can be easily identified as they form white colonies or white sectors in otherwise red colonies. A wild-type, a sml1Δ mutant strain and a strain containing two copies of SML1 (2XSML1) are shown.

(FIG. 3D) The frequency of petite formation was measured in sml1Δ, wild-type and SML1-duplication strains as described in Experimental Details and the averages and standard deviations are shown.

FIGS. 4A–4G. SML1 affects DNA damage sensitivity

Mid-log phase YPD-grown cells were spotted at 10-fold serial dilutions (from $10^5$ to 10 cells) followed by treatment with UV light. At the same time, cells were also spotted onto YPD plates containing HU or MMS at the indicated concentration. These plates and the control YPD plates used to confirm the dilution were incubated at 30° C. for 4 days and photographed. At least two different strains were tested for each genotype. In (FIGS. 4A–C), cells from wild-type, sml1Δ and SML1-duplication strains were examined for their HU and MMS sensitivity. In (FIGS. 4D–G), cells from wild-type, sml1Δ, dun1Δ, dun1Δ sml1Δ strains were tested for UV light, HU or MMS sensitivity.

FIGS. 5A–5K. dNTP pools and the mRNA levels of the RNR genes in sml1 strains (FIGS. 5A–H) The 254 nm absorption profiles of the elution of the dCTP, dTTP, dGTP and dATP peaks are shown in (FIGS. 5A–H). The dNTPs were extracted from W1588-4C (wild-type) and U952-3B (sml1Δ) and separated by a C-18 reverse phase HPLC column (see Experimental Details). An injection volume of 100 μl, which represented 39% of the total dNTP fraction extracted from $3.1 \times 10^9$ cells, was applied. There is no significant difference between the cell volumes of wild-type and sml1 strains. The area under the peaks designated with the arrowheads was integrated to generate the numbers shown in (FIG. 5I) which represent the average of two determinations that differ by only 4%.

(FIG. 5J) Autoradiogram of a blot of total RNA extracted from wild-type, mec1Δ sml1Δ and sml1Δ strains and hybridized with probes specific for RNR1, RNR2, RNR4 and actin.

(FIG. 5K) Autoradiogram of a blot of total RNA extracted from wild-type, sml1Δ, dun1Δ and dun1Δ sml1Δ strains both before and after 3 hour induction with either HU or MMS. The blot was hybridized with probes specific for RNR1, RNR2, RNR3, RNR4 and actin.

FIG. 6. Sml1 and Rnr1 form a complex in vivo

GST-Rnr1 and HA-Sml1 were induced by adding 2% galactose to a mid-log phase yeast culture. Protein was extracted after an additional five hours of growth. Five hundred μg of protein extract was incubated either with glutathione beads or anti-HA antibody followed by protein-G beads as indicated. After washing, the beads were precipitated and the proteins were eluted and separated on a 7.5% SDS-PAGE gel (upper panel) or a 15% SDS-PAGE gel (lower panel). Protein was transferred to membranes and the blots were probed with anti-GST antibody (upper panel) or anti-HA antibody (lower panel). The plasmids carried by the strains are indicated above each lane. The two unlabelled bands in the lower panel are IgG.

Figure 7:
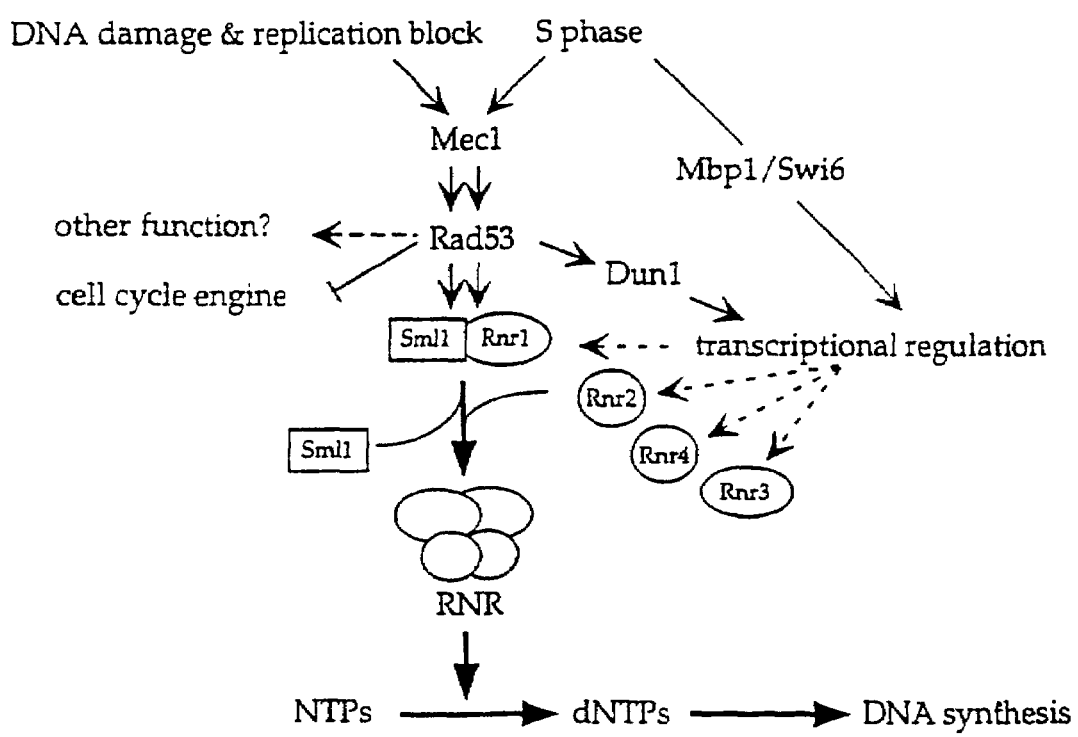

FIG. 7. A model for Mec1 and Rad53 function in RNR regulation

Mec1 and Rad53 are known to function after DNA damage or a DNA replication block(s) to halt cell cycle progression and to up-regulate the transcription of RNR genes through Dun1 as indicated by the thin black lines. Increased transcripts for RNR subunits may result in elevated levels of the corresponding proteins (not yet demonstrated). It is also known that RNR transcripts are induced during S phase, which requires the Mbp1/Swi6 complex (Koch et al., 1993). We propose that post-translational regulation of RNR activity is mediated by removing the inhibitory effect of Sml1. This regulation could occur both during S phase and after DNA damage and requires the function of Mec1 and Rad53. It is likely that the regulation is mediated via the putative Mec1/Rad53 kinase cascade and that the target for phosphorylation could be Sml1 or any of the RNR subunits. The gray arrows indicate S phase regulation and may account for the essential functions of both MEC1 and RAD53. The "other function" of Rad53 is postulated to explain the slower growth of rad53 sml1 double mutants (see FIG. 2D).

Figure 8:
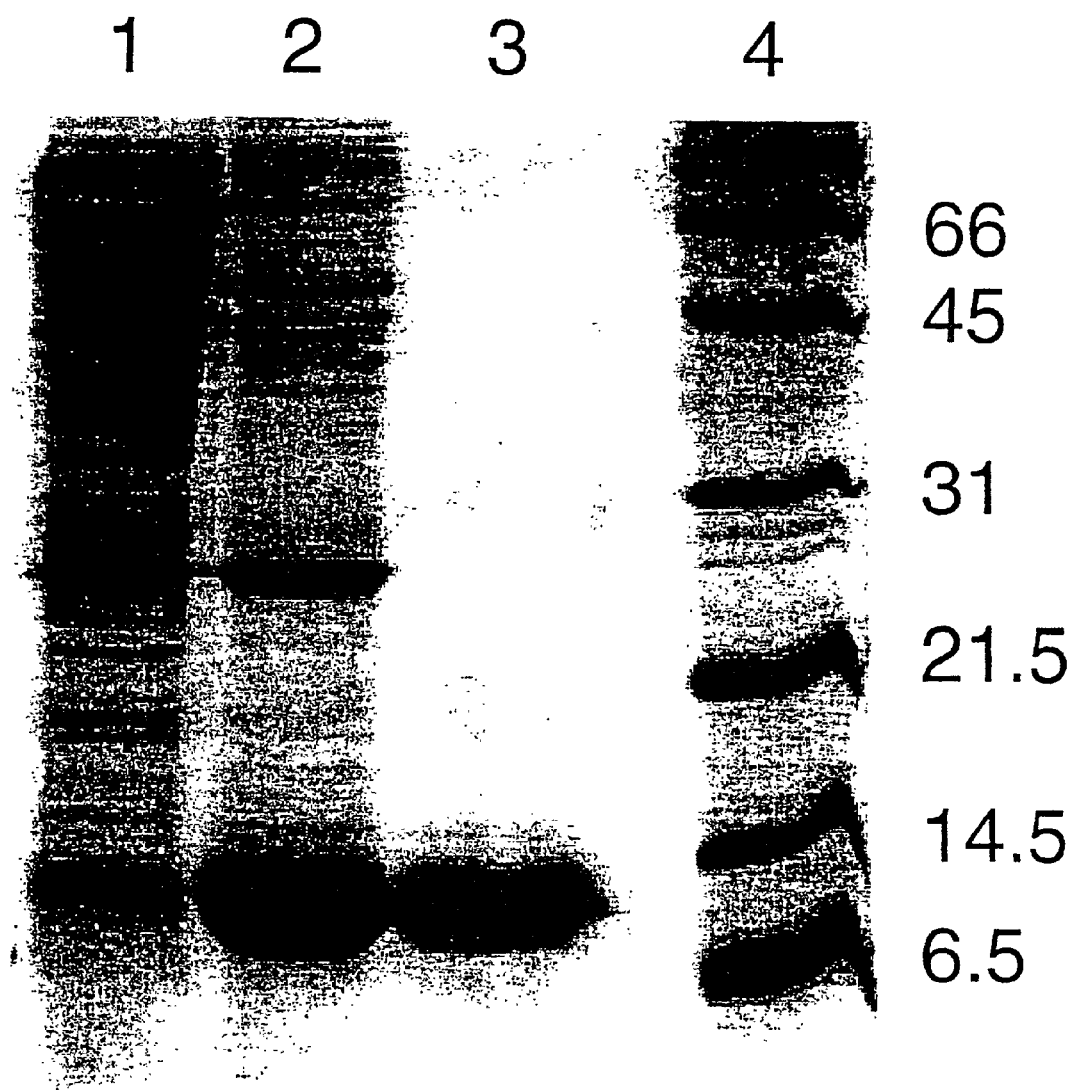

FIG. 8 Samples of Sml1p preparations after different purification steps analyzed on a 15% SDS-PAGE and stained by Coomassie Brilliant Blue. Lane 1; 10 μg of protein lysate after the ultracentrifugation. Lane 2; 10 μg of protein after the ammonium sulfate fractionation. Lane 3; 10 μg of protein after the ultrafiltration. Lane 4; molecular weight markers (kDa).

Figure 9:
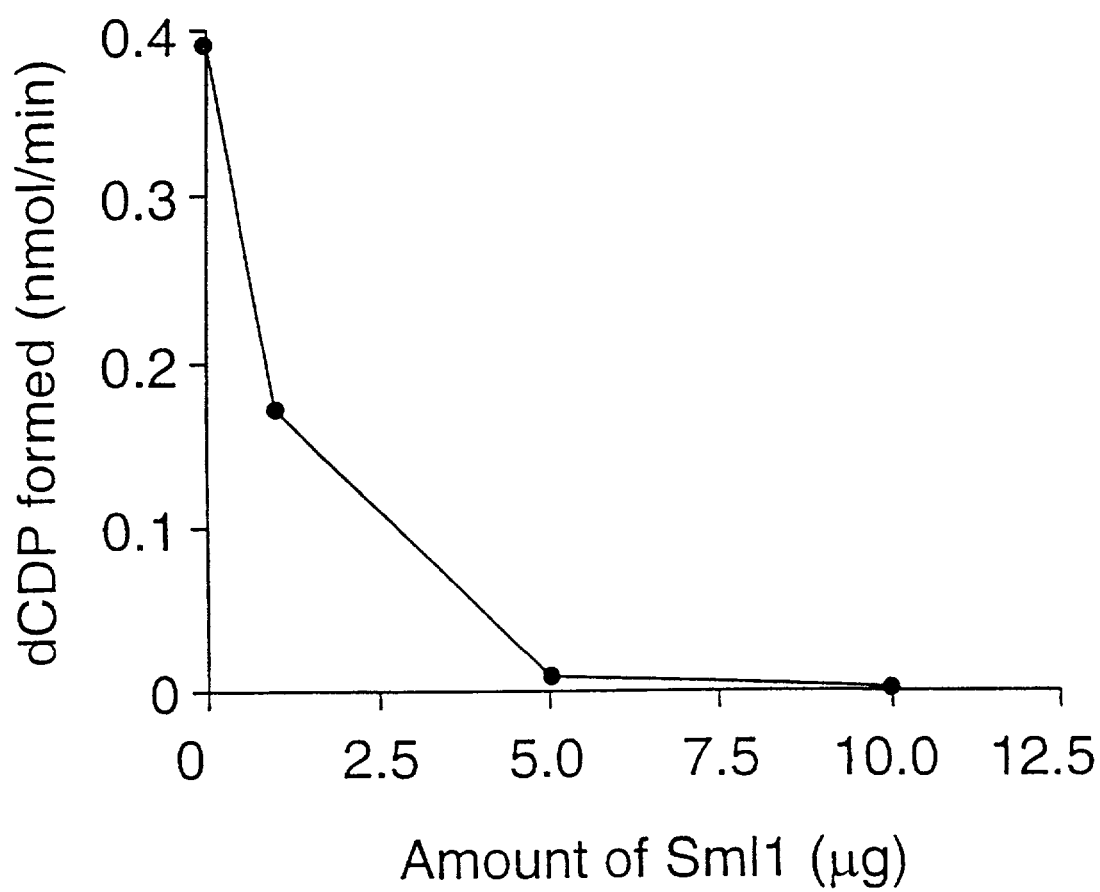

FIG. 9 Inhibition of yeast RNR by Sml1p. A series of tubes containing yeast RNR (10 μg of Rnr1p and 7 μg of Rnr2p/Rnr4p heterodimer) were incubated at 30° C. for 30 min in a final volume of 50 μl: 25 nmol of [$^3$H]CDP (specific activity 37000 cpm/nmol), 2 μmol of Tris-HCl, pH 7.6, 0.125 μmol of ATP, 0.32 μmol of $MgCl_2$, 0.5 μmol of dithiothreitol, 5 μmol of KCl and 1 nmol of $FeCl_3$. In addition, the tubes contained increasing amounts of Sml1p. After incubation, the samples were processed as described earlier to obtain the amount of dCDP formed (22).

Figure 10:
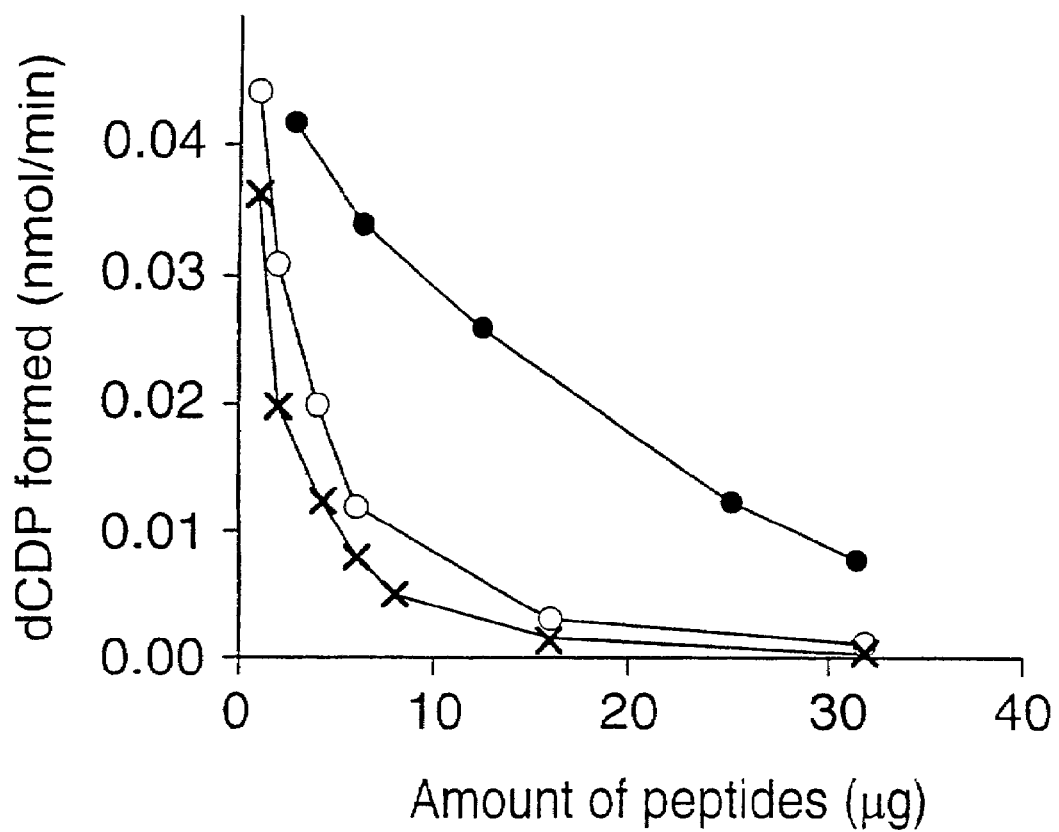

FIG. 10 Inhibition of yeast RNR by nonapeptides corresponding to the C terminal ends of Sml1p, Rnr2p or Rnr4p. A series of tubes containing yeast RNR (10 μg of Rnr1p and 1 μg of Rnr2p/Rnr4p heterodimer) were incubated at 30° C. for 30 min as described in FIG. 9 in the presence of increasing amounts of nonapeptide. Sml1 peptide, ã; Rnr2 peptide, o; Rnr4 peptide, x.

Figure 11:
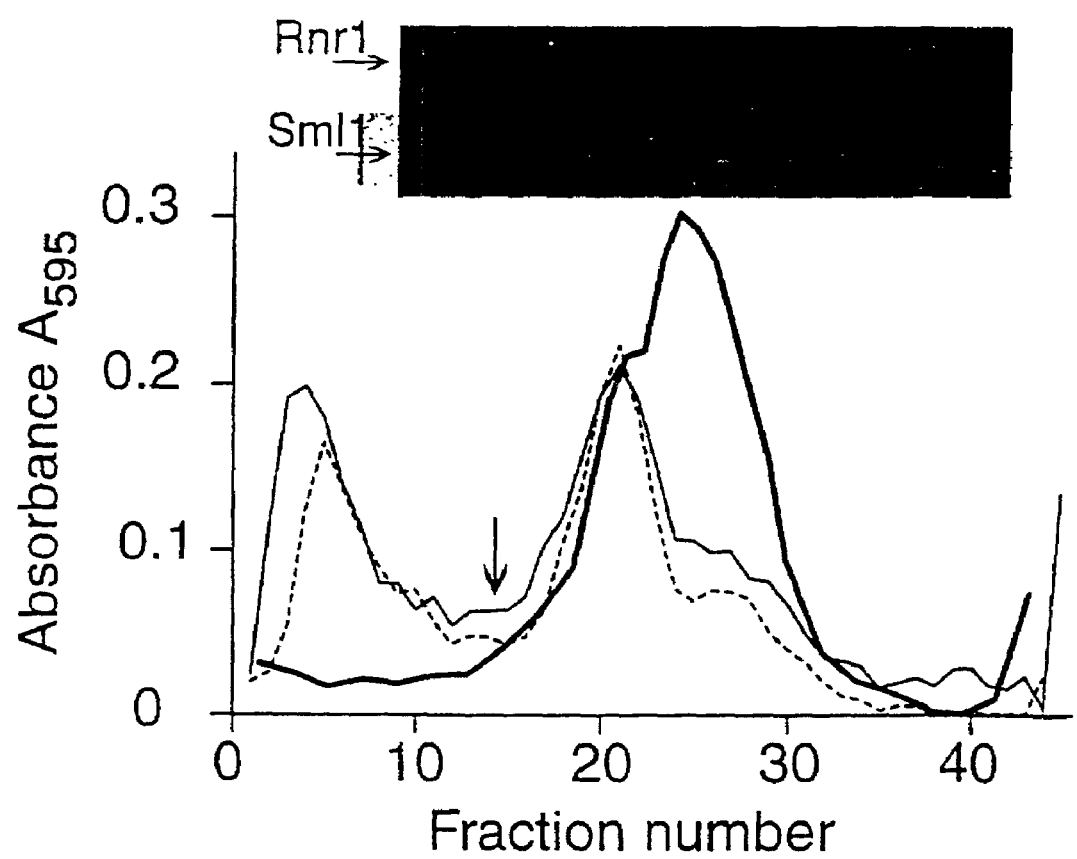

FIG. 11 Sucrose gradient centrifugation of yeast Rnr1p in the absence or in the presence of dTTP, with or without Sml1p. Sedimentation (from the right to the left) was performed as described in Materials and Methods. Catalase ($s_{20,w}$=11.4 S) sedimented in fraction 14 (arrow). Thick line, Rnr1 protein sedimented alone without dTTP or Sml1p. The two peaks represent the dimer (fraction 21) and monomer (fraction 25) positions in the gradient. Hatched line, Rnr1p sedimented in the presence of dTTP. Most of the material now sedimented as tetramers (fraction 5) or dimers (fraction 21). Note that the small peak sedimenting at fraction 26 represents an impurity in the Rnr1p preparation (the band just below the R1 band in the gel insert). The sedimentation of this material is not affected by dTTP. Thin line, Rnr1p with Sml1p sedimenting in the presence of dTTP. SDP-PAGE (15% gel) analysis of fractions from the gradient. Each lane on the gel is positioned above the corresponding fraction in the gradient.

Figure 12A:
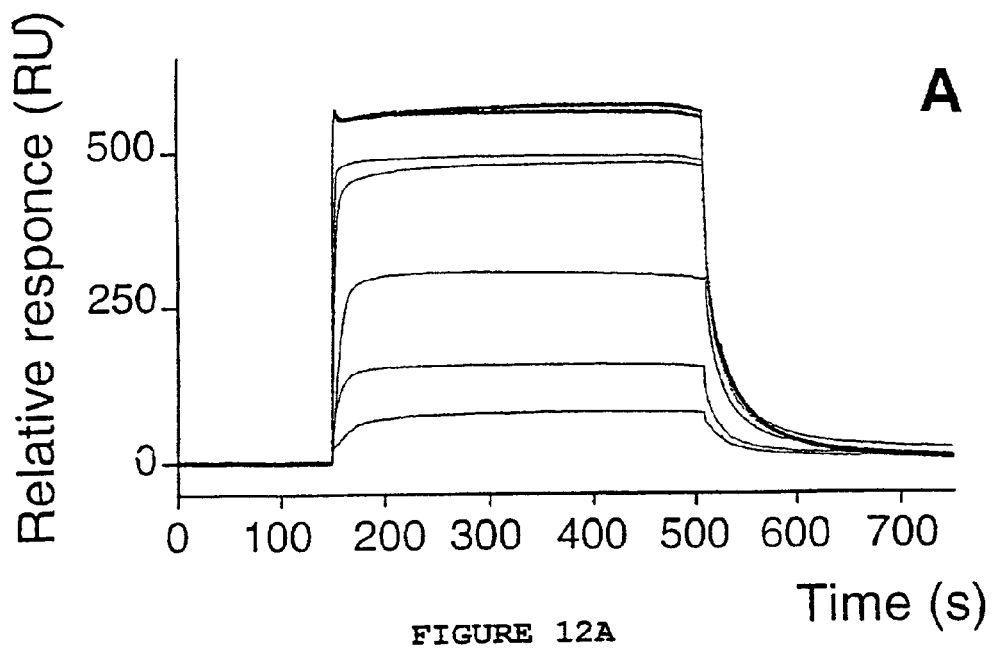

FIG. 12A Sensorgram showing the interaction between immobilized Sml1p (91 RU) and increasing concentrations of mobile phase Rnr1p (0.1, 0.2, 0.25, 0.5, 1, 2 and 2.5 μM using the monomer molecular weight of 100,000). Injection starts at 150 sec and ends at 510 sec. In this figure, the bulk effect response of around 60 RU has been subtracted.

Figure 12B:
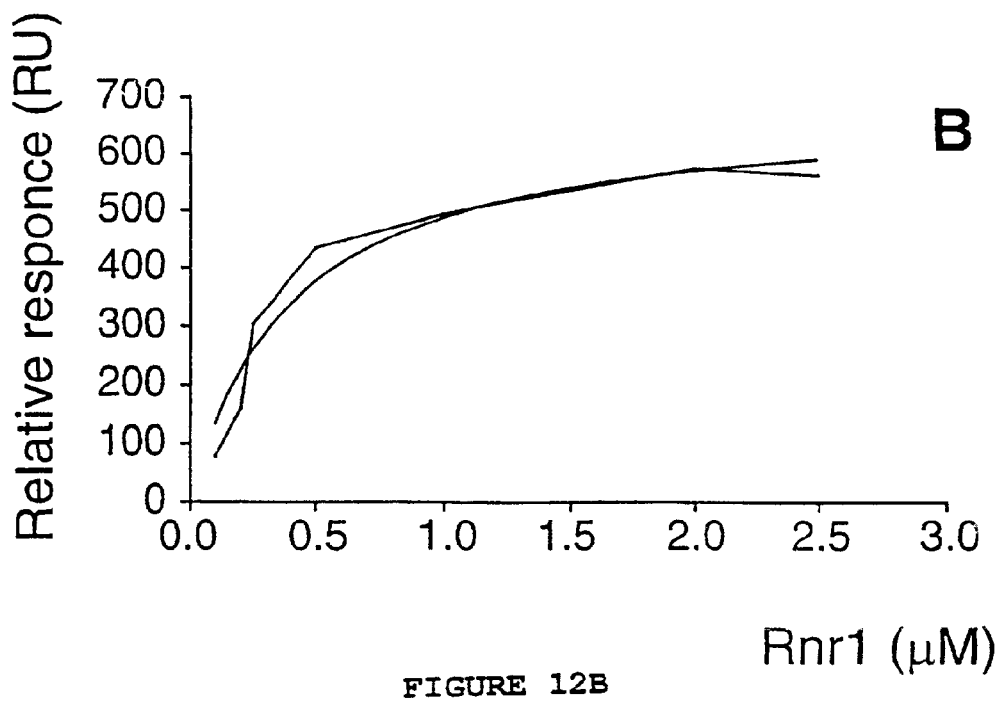

FIG. 12B Dose-response curve where the response at equilibrium is plotted against the concentration of Rnr1p (the same data as shown in A). The plot shows both the experimental curve and a curve fitted to a one site binding model (hyperbola) by the GraphPad Prism program.

Figure 13:
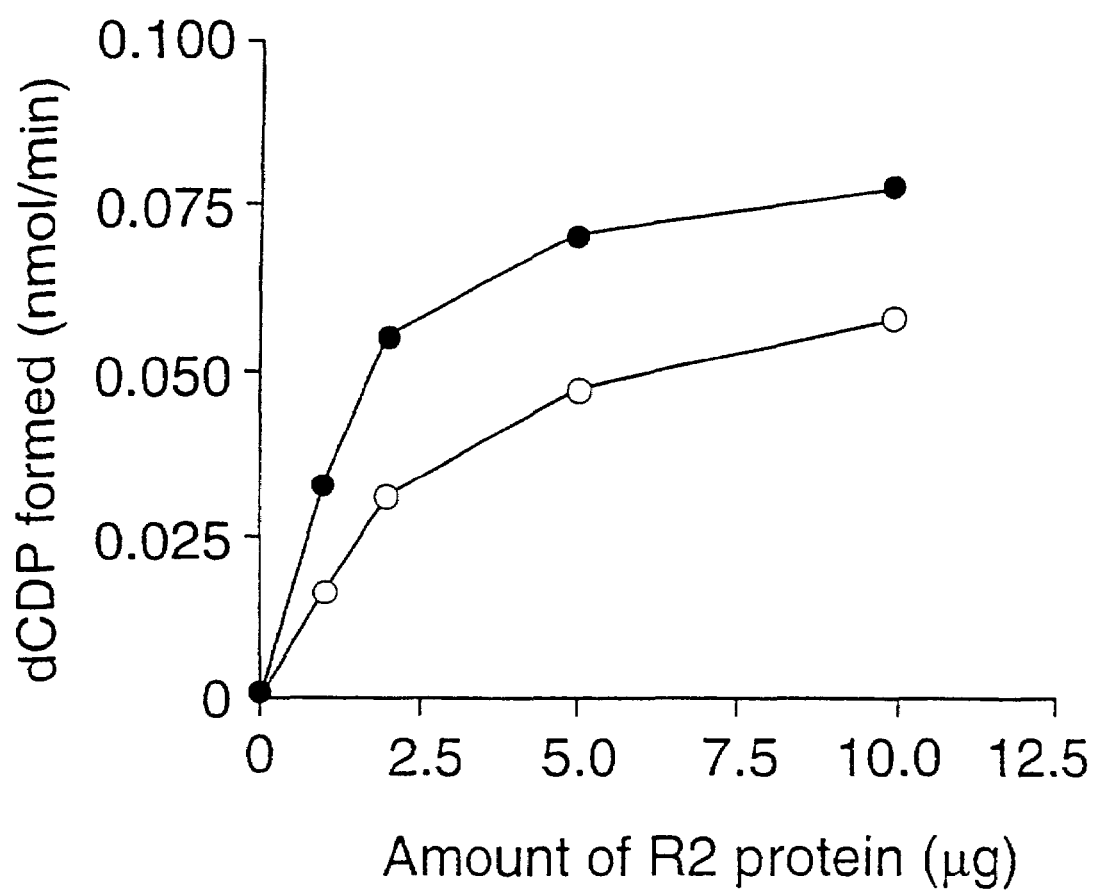

FIG. 13 Inhibition of mouse RNR by the Sml1p. A series of tubes containing mouse RNR (1 μg of R1 protein and the indicated amounts of R2 protein) were incubated at 37° C. for 30 minutes as described in FIG. 9 in the absence (ã) or in the presence of 36 μg of Sml1p (o).

Figure 14:
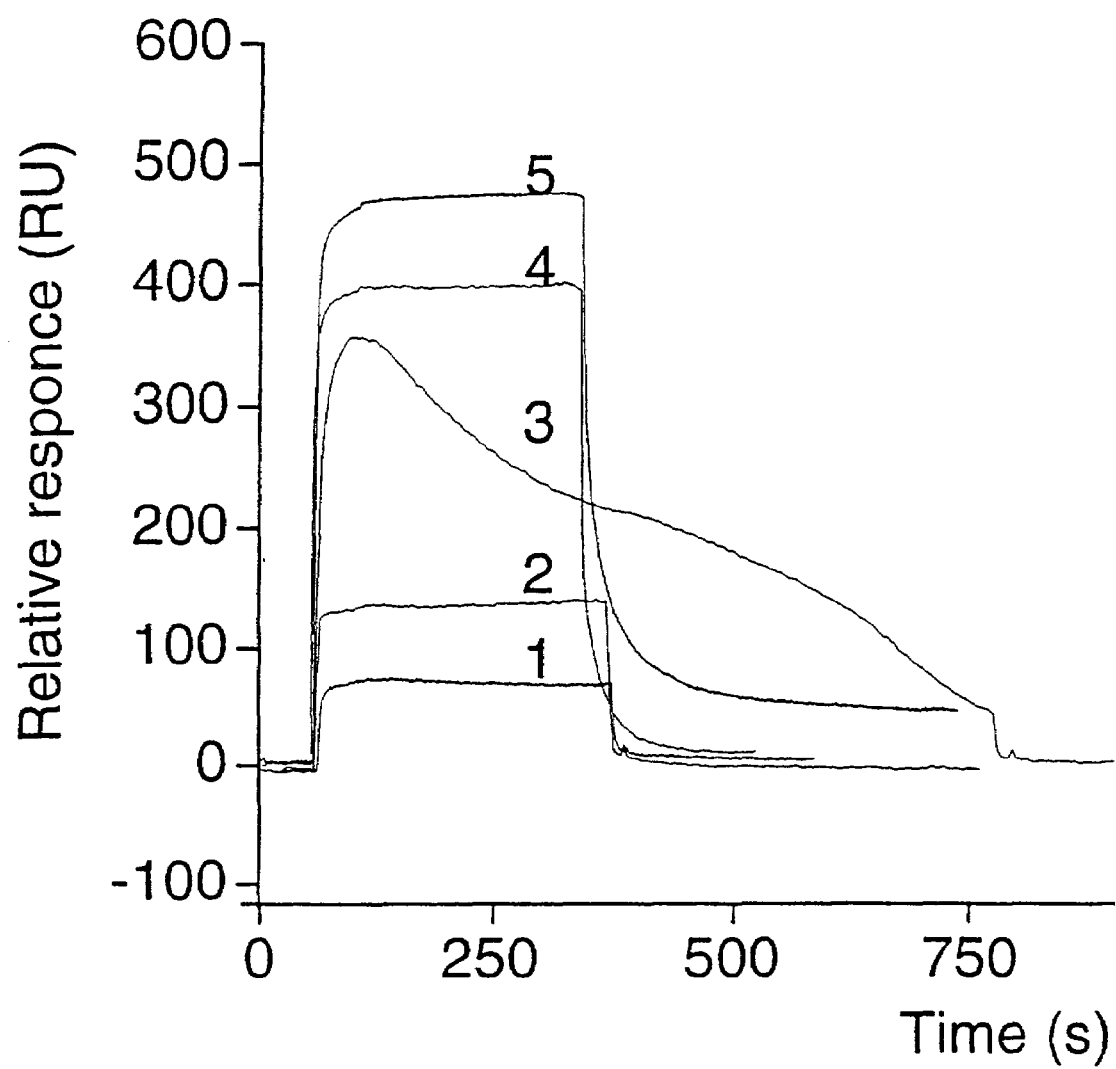

FIG. 14 Sensorgram showing the interaction between immobilized Sml1p and the mouse R1 protein. Curve 1 shows the bulk effect response when R1 protein (0.1 mg/ml) is passed over a sensor chip without Sml1p. Curve 2 shows the response when a mixture of mouse R1 and R2 proteins (both at 0.1 mg/ml) in the presence of 0.1 mM dTTP is passed over a sensor chip with immobilized Sml1p. Curve 3 showes the response with mouse R1 protein alone at 0.1 mg/ml passed over immobilized Sml1p. Note that the injection time for this curve is prolonged from 6 min to 14 min. Curve 4 was obtained with mouse R1 protein at 0.1 mg/ml in the presence of 0.1 mM dTTP passed over immobilized Sml1p, and Curve 5 shows the response obtained with yeast Rnr1p at 0.1 mg/ml passed over immobilized Sml1p.

DETAILED DESCRIPTION OF THE INVENTION

The present invention provides for an isolated Sml1 protein or a homologue thereof. In one embodiment, the Sml1 protein has the amino acid sequence shown in FIG. 1C. In another embodiment, the Sml1 protein is a homologue, such as a human Sml1 protein, a rat Sml1 protein, a mouse Sml1 protein, a microbial Sml1 protein, a plant Sml1 protein, or an insect Sml1 protein.

The present invention also provides for an isolated nucleic acid encoding an Sml1 protein. In one embodiment, the nucleic acid has the nucleotide sequence shown in FIG. 1C. In another example of the present invention, the nucleic acid has the nucleotide sequence which encodes the amino acid sequence shown in FIG. 1C from 1 to 104.

In one embodiment of the present invention, a vector comprises the nucleic acid. The vector may be a virus, a plasmid, a phage or an expression vector.

The present invention also provides for a host cell comprising the vector.

The present invention also provides for a nucleic acid molecule which comprises an antisense sequence of at least a portion of the nucleic acid sequence encoding a Sml1protein.

Furthermore, the present invention encompasses an antibody which specifically recognizes a Sml1 protein. In one embodiment, the antibody is a polyclonal or monoclonal antibody.

The present invention provides for a screening assay for identifying compounds that are capable of reducing the division rate of a cell by altering an interaction between a ribonucleotide reductase and a Sml1 protein in the cell, which comprises: (a) contacting the cell with a compound, (b) comparing the division rate of the cell in step (a) with the division rate of the cell in the absence of the compound so as to determine whether the compound alters the interaction between the ribonucleotide reductase and the Sml1 protein of the cell, thereby reducing the cell division rate of the cell.

In one embodiment of the invention, the compound is an organic compound, a peptide, an inorganic compound, a lipid, a peptidomimetic or a small synthetic compound. In one embodiment, the peptide or the peptidomimetic is a variant of a Sml1 protein or a fragment thereof. In another embodiment of the invention, the fragment is from about 20 amino acids to about 90 amino acids in length. In another embodiment of the invention, the cell is a yeast cell, a mammalian cell, a plant cell, an insect cell or a microbe. In another embodiment of the present invention, the mammalian cell is a human cell, a hamster cell, a mouse cell, a rat cell or a monkey cell.

The present invention provides for a previously unknown compound identified by the screening assay described herein. The present invention also provides for a pharmaceutical composition which comprises the compound identified by the screening assay and a carrier. In one example, the carrier is an aerosol, topical, intravenous or oral carrier, or a subcutaneous implant. In another embodiment, the implant is a time release implant.

The present invention also provides for a method for inhibiting cell division which comprises contacting a cell with a compound identified by the screening assay. The present invention also provides for a method for inhibiting cell division in a subject which comprises administering to the subject an amount of the compound identified by the screening assay.

In one embodiment, the subject is suffering from increased cell division. In another embodiment, the subject is suffering from cancer or a microbial infection. In another embodiment, the subject is suffering from ataxia telangiectasia.

The present invention also provides a method for treating cancer in a cancer patient which comprises adminstering to the patient an amount of a compound effective to increase an interaction between a ribonucleotide reductase protein and an Sml1 protein in cancer cells of the patient, thereby reducing cell division rate of the cancer cells in the patient and treating the cancer.

In another embodiment, the compound may be yeast Sml1 protein which is administered to a cancer patient, wherein the cells of the cancer patient do not express endogenous Sml1 protein. The yeast Sml1 protein is capable of binding to human ribonucleotide reductase protein. In a further embodiment, the compound may also be a synthetic or recombinant Sml1 protein and is administered to a human cancer patient in order to reduce cell division rate of cancer cells. The compound may be yeast Sml1 protein or DNA or RNA encoding yeast Sml1 protein.

The present invention also provides a method for treating a microbial infection in a patient which comprises administering to the patient an amount of a compound effective to increase an interaction between a ribonucleotide reductase protein and an Sml1 protein in the microbe, thereby reducing the division rate of the microbe in the patient and treating the microbial infection.

In one embodiment, the compound is a compound which was identified by the screening assay. In another embodiment, the compound is delivered to the patient via a carrier. In a further embodiment, the carrier is an aerosol, topical, intravenous or oral carrier, or a subcutaneous implant. In a further embodiment, the implant is a time release implant. In another embodiment, the compound is an Sml1 polypeptide or a variant thereof.

Homologs of yeast Sml1 protein and SML1 gene are also encompassed by the present invention. Isolation of homologs in other species once one nucleic acid sequence is isolated in one species (e.g. yeast) is understood to be routine by one of skill in the art. One of skill could isolate the human homolog of Sml1 protein and SML1 gene by routine methods, for example, cloning by computer-determined homology. For example, one could follow the following steps to isolate the human homolog of SML1:

1. PCR amplify the cDNA of human RNR1 gene from a cDNA library. The primers should be able to anneal to the 5' end and 3' end sequence of the human RNR1 ORF and should contain proper restriction enzyme sites to facilitate the cloning.
2. Clone the PCR-amplified fragment into a GBD (Gal4 DNA binding domain) vector, such as pGBD-C1 (James et al., 1996).
3. Transform the pGBD-RNR1 plasmid DNA into a two-hybrid strain, such as PJ69-4A (James et al., 1996).
4. Test the suitability of pGBD-RNR1 plasmid to perform a two-hybrid screen by examining the expression of the GBD-RNR1 fusion protein and its effect on the reporter genes in the two-hybrid strain.
5. Transform GAD (Gal4 DNA activation domain)-based human two-hybrid cDNA library into the two-hybrid strain that contains pGBD-RNR1.
6. Select for the positive interacting plasmid on suitable medium, such as SC-TRP-LEU-HIS and followed by a second round of selection on SC-TRP-LEU-ADE medium.
7. Further test the positives by examining whether the presence of both pGBD-RNR1 and the library plasmid is necessary and sufficient to turn on the reporters of the two-hybrid strain.
8. Isolate the GAD based plasmid DNA from the positive strains and perform sequence analysis on the genes contained within the plasmid. The protein products of such genes should be able to bind to Rnr1. The human homolog of the SML1 gene should be one of those genes. Human homolog of SML1 should be identified by sequence homology to the yeast SML1 nucleic acid sequence.

The present invention provides for variants of the isolated Sml1 protein which may be prepared by introducing appropriate nucleotide changes into a nucleic acid encoding Sml1 or by in vitro synthesis of the desired Sml1 polypeptide. Such variants include, for example, deletions from, or insertions or substitutions of, residues within the amino acid sequence shown in FIG. 1C for yeast Sml1 or similar changes to a homologue of yeast Sml1 protein. Any combination of deletions, insertion, and substitution can be made to arrive at the final construct, provided that the final construct possesses the desired characteristics (e.g., competitive inhibition of RNR). The amino acid changes also may alter post-translational modifications of the Sml1 protein, such as changes in the glycosylation sites or modifying its susceptibility to proteolytic cleavage or phosphorylation.

This invention also provides for fusion proteins which contain a Sml1 polypeptide linked to an unrelated protein domain(s). The fusion proteins may be created by the insertion of amino- and/or carboxyl-terminal fusions ranging in length from one residue to polypeptides containing a hundred or more residues, as well as intrasequence insertions of single or multiple amino acid residues. Intrasequence insertions (i.e. insertions within the Sml1 amino acid sequence) may range generally from about 1 to 10 residues, or preferably 1 to 5, and most preferably 1 to 3. Examples of terminal insertions include Sml1 with an N-terminal methionyl residue (an artifact of the direct expression of Sml1 in bacterial recombinant cell culture), and fusion of a heterologous N-terminal signal sequence to the N-terminus of Sml1 to facilitate the secretion of mature Sml1 from recombinant host cells. Such signal sequences generally will be obtained from, and thus be homologous to, the intended host cell species. Suitable sequences include but are not limited to STII or 1 pp for *E. coli,* alpha factor for yeast, and viral signals such as herpes gD for mammalian cells.

Other insertional variants of Sml1 may include the fusion of the N- or C-terminus to an immunogenic polypeptide, e.g., bacterial polypeptides such as beta-lactamase or an enzyme encoded by the *E. coli* trp locus, or yeast protein, bovine serum albumin, or chemotactic polypeptides.

The present invention also provides for Sml1 polypeptides which have amino acid substitution variants. These variants have at least one amino acid residue in the Sml1 molecule removed and a different residue inserted in its place. The sites of greatest interest for substitutional mutagenesis include a site(s) identified as an active site(s) of Sml1 (e.g. the binding site for RNR), and sites where the amino acids found in Sml1 homolgoues from various species are substantially different or substantially similar in terms of side-chain bulk, charge, and/or hydrophobicity.

Other sites of interest are those in which particular residues of the purified Sml1 polypeptide obtained from various species are identical. These positions may be important for the biological activity of Sml1. These sites, especially those falling within a sequence of at least three other identically conserved sites, are substituted in a relatively conservative manner. Such conservative substitutions may be known as "preferred substitutions" and may include: valine substituted for alanine; lysine for arginine; glutamine for asparagine; glutamate for aspartate; serine for cysteine; asparagine for glutamine, aspartate for glutamate; proline for glycine; arginine for histidine; leucine for isoleucine; arginine for lysine, leucine for methionine, leucine for phenylalanine; glycine for proline, threonine for serine; serine for threonine; tyrosine for tryptophan; phenylalanine for tyrosine and leucine for valine.

Substantial modifications in function or immunological identity of the purified Sml1 polypeptide are accomplished by selecting substitutions that differ significantly in their effect on maintaining (a) the structure of the polypeptide backbone in the area of the substitution, for example as a sheet or helical conformation, (b) the charge or hydrophobicity of the molecule at the target site, or (c) the bulk of the side-chain. Naturally occurring residues are divided into groups based on common side chain properties: hydrophobic; neutral hydrophilic; acidic; basic; residues that influence chain orientation and aromatic. Non-conservative substitutions will entail exchanging a member of one of these classes for another. Such substituted residues may be introduced into regions of Sml1 that are homologous with other proteins, or, more preferably, into the non-homologous regions of the molecule.

One embodiment of the present invention is wherein the compound is a peptidomimetic having the biological activity of Sml1 or wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, cysteine (acetamindomethyl), N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those compounds described herein.

In addition to the compounds disclosed herein having naturally-occurring amino acids with peptide or unnatural linkages, the present invention also provides for other structurally similar compounds such as polypeptide analogs with unnatural amino acids in the compound. Such compounds may be readily synthesized on a peptide synthesizer available from vendors such as Applied Biosystems, Dupont and Millipore.

This invention provides for the creation of a combinatorial library of potential Sml1 homologs that can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see Sambrook, et al., 1989; U.S. Pat. Nos. 5,223,409; 5,198,346 and 5,096,815 which are hereby incorporated by reference in their entireties). The purpose of making such a library is to provide in one mixture, all of the sequences encoding the desired set of potential Sml1 sequences. This mixture could then be used for seletion of particular affinities, binding properties and separate functionalities. Compounds could be generated from this library (i.e. a mixture of peptides) which may be tested in the screening assay described herein in order to identify compounds capable of inhibiting cell division. See Roberts, R. W. and Szostak, J. W. (1997) RNA-epetide fusions for the in vitro selection of peptides and proteins. Proc. Natl. Acad. Sci. USA 94:12297–12302 which is hereby incorporated by reference in its entirety into the present application.

This invention also provides for a replicable vector which contains SML1 sequence and a host cell containing this vector. This expression vector may be a prokaryotic expression vector, a eukaryotic expression vector, a mammalian expression vector, a yeast expression vector, a baculovirus expression vector or an insect expression vector. Examples of these vectors include PKK233-2, pEUK-C1, pREP4, pBlueBacHisA, pYES2, PSE280 or pEBVHis. Methods for the utilization of these replicable vectors may be found in Sambrook, et al., 1989 or in Kriegler 1990 which are incorporated by reference. The host cell may be a eukaryotic cell, a yeast cell, a somatic cell, a germ cell, a neuronal cell, a myocyte, a mammary carcinoma cell, a lung cell, a prokaryotic cell, a virus packaging cell, or a stem cell.

A further embodiment of the invention is a monoclonal antibody which is specific for Sml1. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. Also, they may be used to remove Sml1 from the serum or used to titrate out Sml1 proteins intracellularly. A second advantage of monoclonal antibodies is that they can be synthesized by hybridoma cells in culture, uncontaminated by other immunoglobins. Monoclonal antibodies may be prepared from supernatants of cultured hybridoma cells or from ascites induced by intraperitoneal inoculation of hybridoma cells into mice. The hybridoma technique described originally by Köhler and Milstein, 1976, (hereby incorporated by reference) has been widely applied to produce hybrid cell lines that secrete high levels of monoclonal antibodies against many specific antigens.

This invention provides for a nucleic acid comprising a unique SML1 sequence in a 3' to 5' orientation, antisense to at least a portion of a gene encoding naturally occurring Sml1. This antisense nucleic acid molecule may be labeled with a detectable moiety selected from the group consisting of a fluorescent label, a biotin, a digoxigenin, a radioactive atom, a paramagnetic ion, and a chemiluminescent label. See Inoue et al. U.S. Pat. Nos. 5,208,149 and 5,190,931 and Schewmaker, U.S. Pat. No. 5,107,065 all of which are hereby incorporated by reference.

Labeling of a circular oligonucleotide (such as a replicable vector as described herein) can be done by incorporating nucleotides linked to a "reporter molecule" into the subject circular oligonucleotides. A "reporter molecule", as defined herein, is a molecule or atom which, by its chemical nature, provides an identifiable signal allowing detection of the circular oligonucleotide. Detection can be either qualitative or quantitative. The present invention contemplates using any commonly used reporter molecule including radionucleotides, enzymes, biotins, psoralens, fluorophores, chelated heavy metals, and luciferin. The most commonly used reporter molecules are either enzymes, fluorophores, or radionucleotides linked to the nucleotides which are used in circular oligonucleotide synthesis. Commonly used enzymes include horseradish peroxidase, alkaline phosphatase, glucose oxidase and α-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1.2-phenylenediamine, 5-aminosalicylic acid or toluidine are commonly used. The probes so generated have utility in the detection of a specific nARIA DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al, 1989. This invention also provides a method of amplifying a nucleic acid sample comprising priming a nucleic acid polymerase chain reaction with nucleic acid (DNA or RNA) which includes or is complementary to SML1.

Another embodiment of this invention is the normal expression or overexpression of Sml1 ex vivo in human cells, stem cells or cancer cells or in microbe. The cells may be utilized for gene therapy in patients (See Anderson et al U.S. Pat. No. 5,399,346).

This invention further provides for a transgenic nonhuman mammal whose germ or somatic cells contain a nucleic acid molecule which encodes human or a yeast Sml1 polypeptide or biologically active variants thereof, introduced into the mammal, or an ancestor thereof, at an embryonic stage. This invention provides for a transgenic nonhuman mammal whose cells may be transfected with a suitable vector with an appropriate sequence designed to reduce expression levels of sml1 polypeptide below the expression levels of that of a native mammal. The transgenic nonhuman mammal may be transfected with a suitable vector which contains an appropriate piece of genomic clone designed for homologous recombination. Alternatively, the transgenic nonhuman mammal may be transfected with a suitable vector which encodes an appropriate ribozyme or antisense molecule. See for example, Leder and Stewart, U.S. Pat. No. 4,736,866 for methods for the production of a transgenic mouse.

Biologically functional variants of Sml1 are encoded by nucleic acid molecules which are variants of the SML1 sequence. The foregoing variant DNA sequences may be translated into variant-Sml1 polypeptides which display the biological activity of an Sml1 polypeptide. These variant nucleic acid molecules may also be expressed in this transgenic mammal. Active variants should hybridize to the wild-type SML1 nucleic acid sequence under highly stringent or moderately stringent conditions (Sambrook et al, 1989).

This invention is illustrated in the Experimental Details section which follows. These sections are set forth to aid in an understanding of the invention but are not intended to, and should not be construed to, limit in any way the invention as set forth in the claims which follow thereafter.

Experience Details

EXAMPLE 1

Isolation and Characterization of SML1, a Supressor of a mec1 Mutant

MEC1 is one of the cell cycle checkpoint genes in yeast *S. cerevisiae*. It functions at three points in a mitotic cell cycle: G1 phase, S phase and G2-M phase transition. However, unlike most of the other cell cycle checkpoint genes, such as RAD9, RAD17, RAD24 and MEC3, MEC1 is also essential for vegetative growth. Moreover, certain alleles of mec1 can cause abnormal levels of recombination both mitotically and meiotically. Based on these facts, it has been proposed that Mec1 protein carries out multiple important functions and may connect cell cycle progression, cell growth and recombination. Nevertheless, it is poorly understood how this protein is involved in all of these important cellular processes, and why the cell chooses one protein to control cell growth and to monitor cell cycle progression. There are homologs of Mec1 protein in other organisms, which comprise a new protein family called P13-Kinase family. Many of the family members, such as ATM (ataxia-telangiectacia mutation), Mei-41, Rad3, etc. also carry out multiple roles in the cell. The study of Mec1 protein in yeast may shed light on the physiological roles of other P13-Kinase family members as well as on the understanding of the mechanism of AT.

Here we report the isolation and characterization of one suppressor of mec1 mutants—SML1 (suppressor of mec1 lethality). SML1 was first identified in a mec1-1 strain by genetic analysis, and this allele is called sml1-1. Further genetic assays proved that sml1-1 is a recessive mutation. The gene was cloned using a scheme employing a black/white vector assay. SML1 is located on chromosome XIII. It encodes a small ORF, which was predicted by the Yeast Genomic Project. The search in the database reveals no other homolog in yeast or in any other organisms. Disruption of the chromosomal SML1 gene has no significant effect on cell growth or UV sensitivity. This disruption, like the original sml1-1 allele, completely suppresses the lethality of mec1-1 as well as mec1Δ. Moreover, both sml1-1 and sml1Δ can suppress the lethality of deletion of rad53Δ/mec2Δ and other essential checkpoint genes.

The further study of this suppressor will indicate whether it can also suppress other defects of mec1 mutants and how it can bypass the need of the Mec1 protein for survival. The study of the genetic relationship between SML1 and other suppressors of mec1 lethality may lead to an understanding of the genetic pathway which uses Mec1 protein to control cell growth.

EXAMPLE 2

SML1, a Suppressor of mec1 and rad53 Lethality, Negatively Affects dNTP Synthesis in *Saccharomyces cerevisiae*

MEC1 and RAD53 are two essential genes that are also involved in DNA damage and replication checkpoints in yeast. The exact nature of their essential functions is unknown. Interestingly, ATM and Atm homologs of Mec1 in human and mice respectively, also play dual roles. Mutations in ATM result in a recessive autosomal disease—ataxia telangiectasia (AT). Mitotic cells from AT patients and Atm-/- mice grow poorly, senesce prematurely and require more nutrients in vitro. The growth defect of the Atm -/- cells correlates with a failure to enter S phase efficiently and can be suppressed by deleting p53 or p21. The molecular basis for the cell growth function of ATM and Atm is not clear. Given the conservation between these proteins, investigating the mitotic growth function of Mec1 in yeast may shed light on that of ATM and Atm.

Rad53 is a nuclear-localized protein kinase, functioning downstream of Mec1 in the chekpoint pathways. Overproducing RAD53, DUN1 or TEL1 suppresses the lethality of mec1Δ, suggesting that these genes may function downstream of MEC1 or in redundant but minor pathways in cell growth.

Herein is reported the identification and characterization of a mutation, sml1, that permits cell growth in the absence of Mec1 and Rad53. Suppression of mec1 lethality by sml1 does not require the function of Rad53, Dun1 or Tel1. The SML1 gene encodes a novel protein with no known homolog in yeast or any other organism. We found that sml1 strains are more resistant to DNA-damaging agents. In addition, deletion of the SML1 gene suppresses the sensitivity of dun1 mutants to DNA damage. It also affects mitochondrial biogenesis in an analogous manner to over-expressing the large subunit of ribonucleotide reductase (Rnr1). Both two-hybrid and co-immunoprecipitation experiments show that Sml1 binds to Rnr1 in vitro and in vivo. Furthermore, direct measurement of the dNTP pools reveals an increase in sml1Δ, strains. Based on these results, we propose that Sml1 inhibits dNTP synthesis post-transcriptionally by binding directly to Rnr1 and that Mec1 and Rad53 are required to relieve this inhibition at S phase.

EXAMPLE 3

DNA Damage, Repair and Recombination in *S. cerevisiae*

DNA damage recognition often elicits a pause in the cell cycle, a response that is termed a checkpoint. Mutants of many of the genes that control these checkpoints are radiation sensitive. Two such genes are MEC1 and RAD53. Both are required in all DNA damage and replication cell cycle checkpoint pathways in G1, S and G2 phases to ensure correct transmission of the genetic material. In the face of DNA damage or DNA replication blockage, mec1 and rad53 mutants fail to arrest the progression of the cell cycle and fail to induce several DNA repair genes, including the ribonucleotide reductase genes (RNRs). In addition to their involvement in checkpoint pathways, Mec1 and Rad53 are both essential for cell growth. This property distinguishes them from the majority of other checkpoint genes, which are dispensable for cell growth. Although the terminal morphology of mec1 and rad53 cells implies that they likely function in S phase, the exact nature of the essential functions of the Mec1 and the Rad53 proteins is unknown.

To understand the molecular basis of the essential functions of Mec1 and Rad53, we identified and characterized a mutation, sml1, which permits cell growth in the absence of these two proteins. SML1 acts downstream of genes whose overexpression can suppress mec1 deletions. In addition, sml1 affects various cellular processes in a manner similar to the overproduction of the large subunit of ribonucleotide reductase, RNR1. These include an effect on mitochrondrial biogenesis, on the DNA damage response and on cell growth. An increase in Rnr transcription does not account for these effects. In vivo and in vitro experiments show that Sml1 binds to Rnr1. Thus, Sml1 inhibits dNTP synthesis post-transcriptionally by binding directly to Rnr1 and that Mec1 and Rad53 are required to relieve this inhibition at S phase.

EXAMPLE 4

A Novel Protein is Identified in Yeast

In a genetic study, a protein in yeast was identified that interacts by binding to the largest subunit of ribonucleotide reductase (Rnr1). The binding causes negative regulation of RNR function and it is the only known protein to do so. The protein is encoded by a novel gene assigned the name YML058w by the yeast genomic project at Stanford. This protein has been named herein Sml1. The Sml1 protein is 104 amino acids long.

The subunits of yeast RNR are closely related to those in humans, at the primary and secondary structure level. It is therefore likely that a human homologue of SML1 and Sml1 exists. Based on the biological property displayed by the yeast Sml1 protein, the human homologue can then be isolated. The yeast Sml1 protein genetically interacts with Mec1, a homolog of ATM in humans. The ATM gene is mutated in individuals that have ataxia-telangiectasia, a cancer-prone syndrome. In addition, ATM mutations are among the most common heterozygous mutations in the population. Thus, the isolation of the human SML1 gene will help in the elucidation of the function of ATM and the potentially lead to new cancer and disease therapies.

RNR is present in all cells and is the enzyme that converts NTPs to dNTPs. It regulates the pool size of precursors for both mitochondrial and nuclear DNA synthesis and its activity is required for cell division. In proliferating cancer cells, RNR activity is dramatically higher compared to normal cells. This difference makes RNR a desireable target for cancer treatment. Several chemotherapeutic drugs including thiosemicarbazones, hydroxyurea, 2,3-dihydro-1H-pyrazole [2,3]-alimidazole (IMPY) and several other antitumor agents have been developed (Cory, J. G., et al. Adv. Enzyme Regul. 1985, 23:181–192; Matsumoto, M. et al. Cancer Chemother. Pharmacol. 1990, 26:323–329; Carter, G. L. et al. Cancer Res. 1988, 48:5796–5799; Matsumoto, M. and Cory, J. G. Proc. Am. Assoc. Cancer Res. 1989, 30, A2431). Hydroxyurea is the most relevant clinically. However, these drugs do not only target cancer cells, they also generally are toxic to the body.

One example of a new approach to the design of an anti-cancer drug is the use of peptides that can target cancerous tissue. In this approach, a small peptide that binds directly to cancer cells is identified. See Arap, W. et al. (1998) Cancer treatment by targeted drug delivery to tumor vasculature in a mouse model. Science 279:377–380 which is hereby incorporated by reference in its entirety into the present application. This allows exquisite targeting of cancer cells. By fusing this peptide to another specific peptide that could inactivate a cellular process, only the cancer cells are killed. This overcomes one of the major problems encountered by chemical drugs, namely thier toxicity to normal growing cells.

A Sml1-like protein in humans could be used to design an inhibititor of RNR activity. The property of such an inhibitor-linked peptide drug would be to bind RNR and eliminate its activity. For this approach to be feasible, the size of these peptides should be as small as possible. Therefore, the small size of the Sml1 protein makes it a good candidate for further development.

In addition, insight gained about the protein interaction between Sml1 and Rnr1 may lead to the design of new assays or methods to develop and identify compounds that act as inhibitors of disease-causing microorganisms. The present invention provides a novel protein useful for the development of assays to identify antimicrobial drugs and anti-cancer drugs as well as to identify similar proteins in other species.

The present invention is useful for the following: (1) the Sml1 protein may be used in assays to identify effective anti-cancer peptide drugs which are able to target cancerous tissue; (2) Study of the Sml1 protein will aid in a better understanding of ATM function, which is important since ATM mutations are among the most common heterozygous mutations in the population known to cause human cancer; (3) the present invention is also useful in that a strategy is provided to clone the SML1 gene from other species and from micro-organisms which may lead to novel assays to fight diseases caused by the corresponding micro-organism.

The invention provides the understanding of a new layer of regulation of RNR that can be exploited in screening assays to identify novel nucleic acid constructs or other types of compounds that target this enzyme in order to inhibit RNR activity or to increase RNR activity. The present invention also provides an understanding of the essential function of MEC1 and RAD53 to provide a model for how ATM works in humans.

EXAMPLE 5

A Suppressor of Two Essential Checkpoint Genes Identifies a Novel Protein that Negatively Affects dNTP Pools In *Saccharomyces cerevisiae,* MEC1 and RAD53 are essential for cell growth and checkpoint function. Their essential role in growth can be bypassed by deletion of a novel gene, SML1, which functions after several genes whose overexpression also suppresses mec1 inviability. In addition, sml1 affects various cellular processes analogous to overproduction the large subunit of ribonucleotide reductase, RNR1. These include effects on mitochondrial biogenesis, on the DNA damage response and on cell growth.

Consistent with these observations, the levels of dNTP pools in sml1Δ strains are increased compared to wild-type. This effect is not due to an increase in RNR transcription. Finally, both in vivo and in vitro experiments show that Sml1 binds to Rnr1. We propose that Sml1 inhibits dNTP synthesis post-translationally by binding directly to Rnr1 and that Mec1 and Rad53 are required to relieve this inhibition.

In the yeast *Saccharomyces cerevisiae*, the Mec1 and Rad53 proteins are involved in the G1, S and G2 cell cycle checkpoint pathways (reviewed by Elledge, 1996). In the presence of DNA damage or a DNA replication block(s), these proteins are required to arrest or slow cell cycle progression. At the same time, they induce transcription of the genes encoding ribonucleotide reductase (RNR), which catalyzes the rate-limiting step in dNTP synthesis that is necessary for replication and repair (reviewed by Reichard, 1988). In addition to their involvement in checkpoint pathways, Mec1 and Rad53 are both essential for cell growth (Zheng et al., 1993; Kato and Ogawa, 1994). This property distinguishes them from most other checkpoint genes, which are dispensable for growth.

Two observations suggest that Rad53 acts after Mec1 for both checkpoint and essential functions. First, the phosphorylation of Rad53 in response to DNA damage is absent in a mec1 mutant (Sanchez et al., 1996; Sun et al., 1996). Second, overproduction of Rad53 suppresses mec1 lethality and partially suppresses its hydroxyurea sensitivity (Sanchez et al., 1996). Since both proteins function as signal transducers in a common checkpoint pathway, they may play a similar role in the regulation of mitotic cell growth. However, the exact nature of their essential functions is not known and whether their checkpoint and cell growth functions overlap is still an open question.

Mec1 is a member of the PI3-kinase family, composed of proteins that have PI kinase or protein kinase activity (reviewed by Zakian, 1995; Shiloh, 1997). Interestingly, ATM and Atm, homologs of Mec1 in human and mice respectively, also play dual roles in cell growth and cell cycle checkpoint function (reviewed by Friedberg, 1995; Shiloh, 1997). Mutations in the ATM gene result in a recessive autosomal disease, ataxia telangiectasia (AT), a multi-system disorder associated with a high risk of cancer. Mitotic cells from AT patients grow poorly, senesce prematurely and exhibit a higher nutrient requirement in vitro. In addition, these cells are checkpoint deficient since they are sensitive to ionizing radiation and display radioresistant DNA synthesis. The phenotype of Atm-deficient mice mimics that of AT patients, and fibroblasts from these mice exhibit growth defects and radioresistant DNA synthesis similar to that observed in AT cells (Barlow et al., 1996; Xu et al., 1996; Xu and Baltimore, 1996; Elson et al., 1996). The growth defect of the Atm-deficient cells correlates with a failure to enter S phase efficiently and can be suppressed by deletion of either the p53 or p21 gene (Xu and Baltimore, 1996; Westphal et al., 1997; Wang et al., 1997b). The molecular basis for the cell growth functions of ATM and Atm is not clear. Given the conservation between Mec1 and these two proteins, an investigation of the role of Mec1 in mitotic growth may shed light on the cell growth functions of ATM and Atm.

To understand the essential functions of Mec1 and Rad53, we identified and characterized a mutation, sml1, which allows cell growth in the absence of Mec1 and Rad53 proteins. Sml1 acts after Dun1 and Tel1 (overexpression of either also rescues mec1 lethality; Nasr et al., 1994; Morrow et al., 1995; Sanchez et al., 1996). Several aspects of the phenotype of strains with a disrupted SML1 gene can be mimicked by overexpressing the large subunit of ribonucleotide reductase (Rnr1). This suggests that Sml1 negatively affects dNTP synthesis, an essential process that is tightly regulated at multiple levels during the cell cycle and in response to DNA damage. Furthermore, we found that Sml1 binds to Rnr1 suggesting that it exerts its effect through inhibitory binding to Rnr1. Based on our results, one possible explanation for the essential functions of Mec1 and Rad53 is that they are required to remove the inhibitory effect of Sml1 on dNTP synthesis during S phase to facilitate DNA replication.

Results

The identification of sml1-1 in mec1-1 strains

During a genetic analysis of a mec1-1 strain, we found that one quarter of the spores are inviable (Table 1). This is true when the strains were crossed into various genetic backgrounds including W303, SK1, S288C and A364a (the parental strain of the original mec1-1 isolate). In all cases, most of the MEC1 spores are viable (89% –96%) however only half of the mec1-1 spores are able to form colonies (Table 1). The simplest interpretation is that a suppressor mutation is segregating in these crosses and that the mec1-1 spores are viable only in the presence of this unlinked mutation. Similar observations consistent with this view have been reported in the A364a background (Paulovich et al., 1997).

Next, we identified wild-type MEC1 segregants that contain the suppressor and crossed them to mec1-1 viable spores. Genetic analysis showed that all of the mec1-1 spores from these diploids are viable, confirming that the suppressor maps to a single locus. Finally, a plasmid containing the MEC1 gene fully suppresses mec1-1 lethality, indicating that the inviability of mec1-1 is caused by mutation of the MEC1 gene and not any other linked essential genes. We conclude that mec1-1 is viable only in the presence of an unlinked suppressor. We named the suppressor sml1-1, for suppressor of mec1 lethality.

Cloning SML1

Before cloning the SML1 gene, we determined that the sml1 mutation was recessive (see Experimental Procedures). Based on this result, we developed a cloning scheme employing a red/white sectored colony method (FIG. 1A). Briefly, we constructed an indicator strain by introducing a plasmid containing ADE3 and MEC1 into a white ade2Δ ade3Δ mec1-1 sml1-1 strain. This plasmid confers red color to the colony by providing the Ade3 protein in trans (Roman, 1956). Cells growing in the absence of selection for this plasmid form red/white sectored colonies as the plasmid is not needed for viability and is lost at a high rate, ($10^{-2}$–$10^{-3}$, Koshland, 1985). We expected that introduction of a SML1-complementing plasmid would result in solid red colonies since the resident ADE3-MEC1 plasmid would now become indispensable for cell growth. After transformation with a CEN-LEU2 plasmid-based genomic library into the indicator strain, candidate clones were identified as solid red colonies on leucine-less medium and false positives were discarded after the secondary screen described in Experimental Procedures.

Two plasmids containing the identical 9 kb insert were identified after the screen. A genetic analysis showed that the cloned region and SML1 are tightly linked (see Experimental Procedures). Sequence analysis revealed that the insert contains two full length ORFs: YML059C and YML058W, and most of the CMP2 gene on chromosome XIII (Cherry et al., 1997). Plasmids deleted for most of the CMP2 and YML059C genes can still complement a sml1-1 mutation.

However, a YML058W-disrupted plasmid fails to complement sml1-1 strains (FIG. 1B), indicating that the YML058W ORF is the SML1 gene. This ORF is capable of encoding a novel, 104 amino acid long protein (FIG. 1C) and no other homologs of Sml1 have been identified thus far.

sml1 Mutations Rescue mec1 Lethality, but Not DNA Damage Sensitivity

Figure 1B:
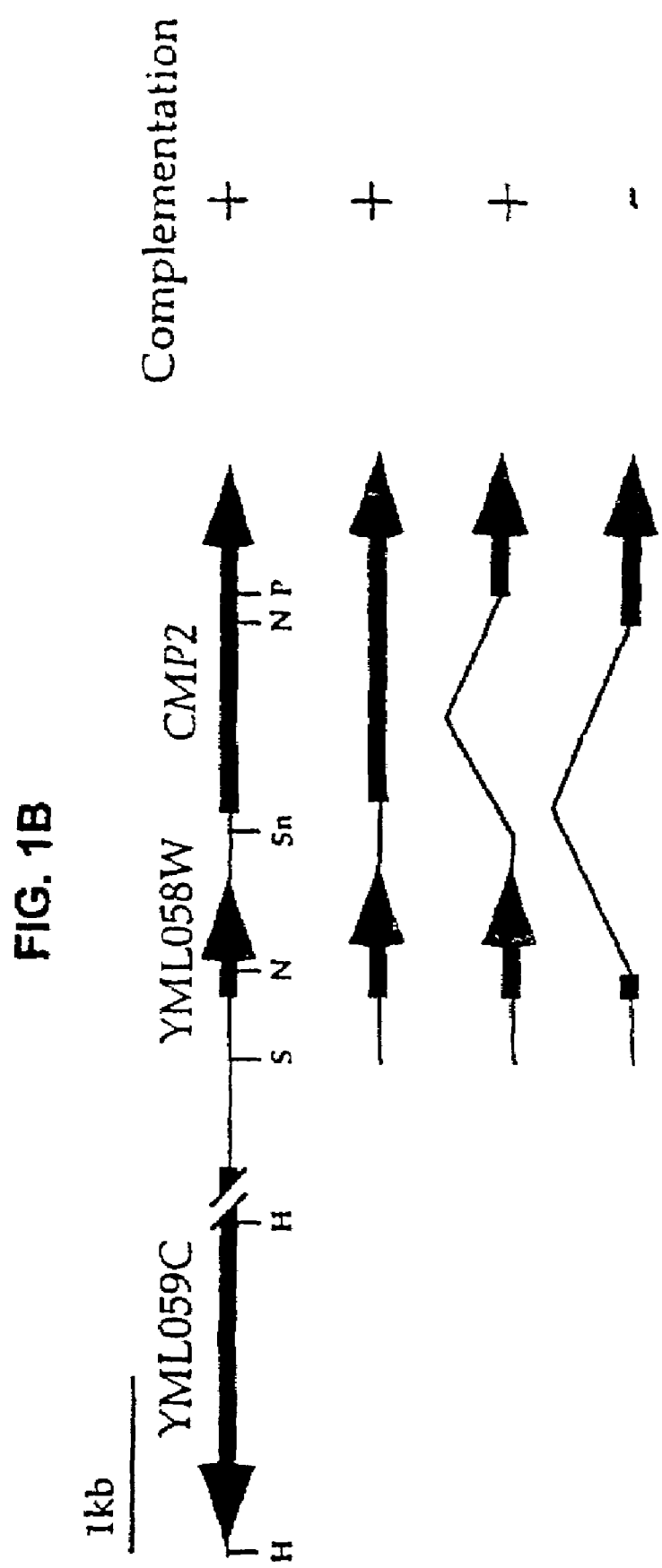
Figure 2A:
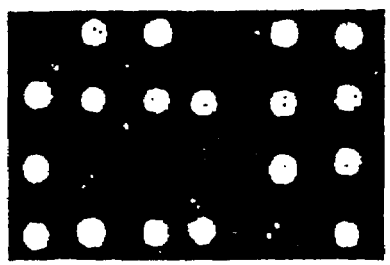
FIGS. 2A–2D. Suppression of the lethality of mec1Δ and rad53Δ by sml1 mutations (FIGS. 2A–2D) The genotype of the diploid is indicated above each panel. Six tetrads are shown for each and spore clones from the same tetrad are displayed vertically. In all cases, the genotype of inviable spores is deduced from those of the sister spore clones and are mec1Δ in (FIGS. 2A, 2B & 2C) and rad53Δ in (FIG. 2D). In (FIG. 2A), wild-type, sml1Δ and mec1Δ sml1Δ spore clones are shown to grow equally well. In (FIG. 2B), dun1Δ, sml1Δ dun1Δ, and mec1Δ sml1Δ dun1Δ triple mutant spores clones grow like wild-type. In (FIG. 2C), the two slow-growing spore clones are mec1Δ sml1Δ tel1Δ triple mutants. In (FIG. 2D), the uniformly slow-growing spore clones are rad53Δ sml1-1 double mutants.

DNA sequence analysis revealed a 290 bp deletion in sml1-1 strains upstream of the SML1 ORF. This deletion lies between two 11 bp direct repeats in the promoter region and includes the hypothetical consensus TATA box of SML1 (FIG. 1C). No alteration of the ORF region in sml1-1 mutant strains was detected. Next, we generated a null allele by replacing the SML1 ORF with a HIS3 marker. Like sml1-1 strains, the sml1Δ does not exhibit a growth defect. Both alleles completely rescue the lethality of mec1-1 or mec1Δ strains (FIG. 2A). Thus, it is likely that the loss of the TATA box in sml1-1 creates a null allele since its phenotype is indistinguishable from that of a complete deletion of the SML1 ORF.

We examined the effect of sml1-1 and sml1Δ on DNA damage sensitivity in both mec1Δ and mec1-1 strains. We found that all four strains show similar sensitivities to hydroxyurea (HU), ultraviolet light (UV) and methyl methanesulfonate (MMS), while both sml1-1 and sml1Δ strains on their own are not sensitive to these agents (described below). In addition, sml1Δ does not rescue the DNA damage sensitivity of mec1-3 and mec1-8, two mutant strains that do not require sml1 for viability. Thus, sml1 mutations do not rescue the DNA damage sensitivity of mec1 strains, although they do rescue mec1 inviability.

Interactions between SML1, RAD53, TEL1 and DUN1

Figure 2B:
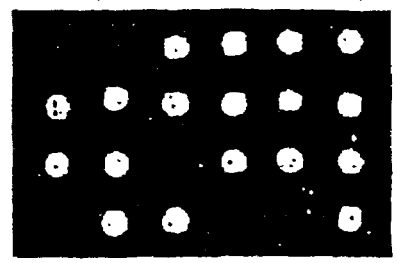
Figure 2C:
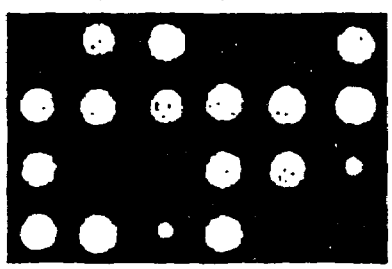

Overexpression of any one of three genes, RAD53, TEL1 and DUN1 can suppress the lethality of mec1Δ (Nasr et al., 1994; Morrow et al., 1995; Sanchez et al., 1996). We tested whether sml1 suppression of mec1 is dependent on the product of any of these genes by examining the viability of mec1 sml1 strains in the absence of each gene. We found that mec1Δ sml1Δ dun1Δ and mec1Δ sml1Δ tel1Δ strains are viable (FIGS. 2B & 2C). The mec1Δ sml1Δ dun1Δ triple mutants grow as well as wild-type and sml1Δ dun1Δ double mutants, while mec1Δ sml1Δ tel1Δ triple mutants grow more slowly than both wild-type and sml1Δ tel1Δ strains. This indicates that sml1 suppression does not depend on the function of either Dun1 or Tel1. However the slow growth of mec1Δ sml1Δ tel1Δ triple mutants shows that Tel1 is important for the growth of mec1 sml1 strains. A synergistic effect of Mec1 and Tel1 on cell growth has also been observed in another genetic background (Morrow et al., 1995) and may indicate a functional redundancy between these two proteins.

Figure 2D:
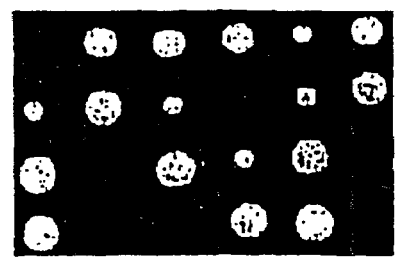

At first, it appeared that a similar set of genetic experiments could not be performed on a rad53Δ strain, since it is inviable. However, we found that rad53Δ sml1 and rad53Δ mec1Δ sml1 strains are viable and that they both grow more slowly than wild-type and mec1Δ sml1Δ double mutants (FIG. 2D). Thus, loss of Sml1 not only makes Mec1 dispensable for cell growth, but also rescues the lethality of rad53Δ strains. This also demonstrates that sml1 suppression of mec1 is not dependent on the activity of Rad53. Finally, as is the case for mec1, the suppression of rad53Δ by sml1 does not require Dun1 or Tel1 (data not shown).

Deletion of SML1 differentially affects mec1Δ and rad53Δ strains as judged by the growth of the double mutants (FIGS. 2A & D). This implies that Mec1 and Rad53 may have some non-overlapping roles during cell growth. Although overexpression of Rad53 rescues mec1 lethality (Nasr et al., 1994), we found that the converse is not true (see Experimental Procedures). Furthermore, our results show that rad53 is epistatic to mec1 since rad53Δ mec1Δ sml1 strains grow like rad53Δ sml1 mutants and not like mec1 sml1 mutants. Taken together, these results indicate that Rad53 likely acts after Mec1 for its role in growth and that it may have an additional function(s) independent of Mec1.

Sml1 Affects Mitochondrial Propagation

Figure 3A:
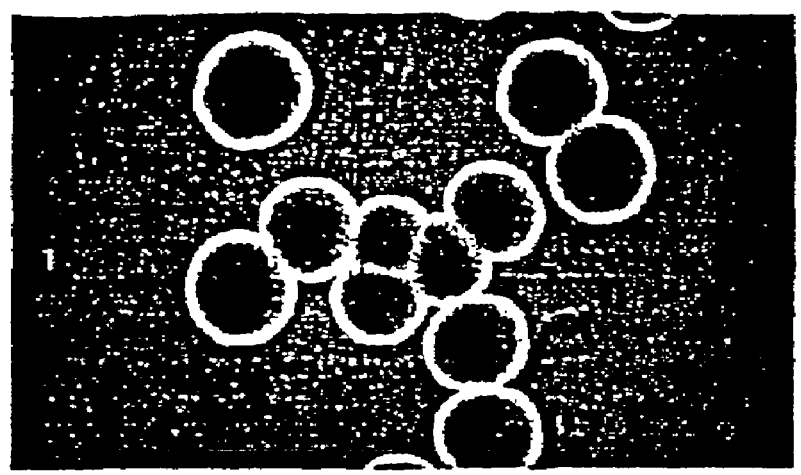
Figure 3B:
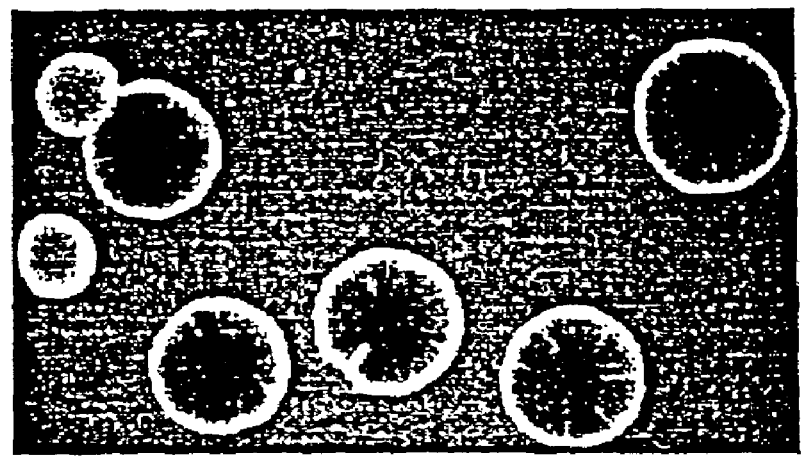

In addition to its interaction with mec1 and rad53, the only noticeable phenotype of sml1 strains is a decrease in the frequency of petite formation. In yeast, petite colonies are formed by cells that do not contain functional mitochondria and cannot grow on a non-fermentable carbon source. In our W303 genetic background, petites are easily identified as slow-growing white colonies (FIG. 3A). We found that the frequency of petite formation in sml1Δ strains is 2.3-fold lower than that of wild-type strains. In contrast, expression of an extra copy of SML1 causes a 3.5-fold higher frequency (FIG. 3B). Thus, the frequency of petite formation is positively correlated with the copy number of the SML1 gene.

Figure 3C:
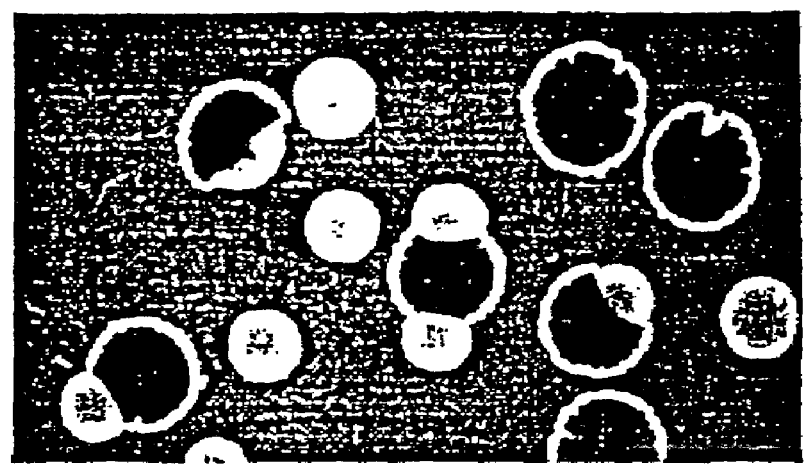
Figure 3E:
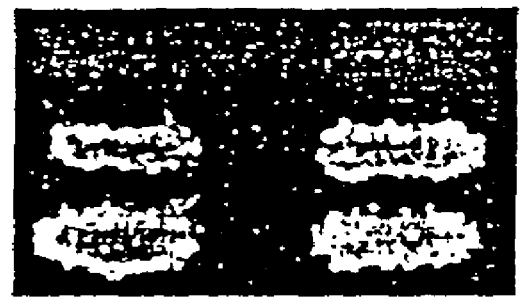
(FIG. 3E) sml1Δ rescues the lethality of mip1-1 strains at 37° C. Patches of cells with the indicated genotypes were grown at 30° C. on selective medium before replicating to YPGlycerol medium. The replicated plate is shown after overnight incubation at 37° C.
Figures 5E, 5F, 5G, 5H:
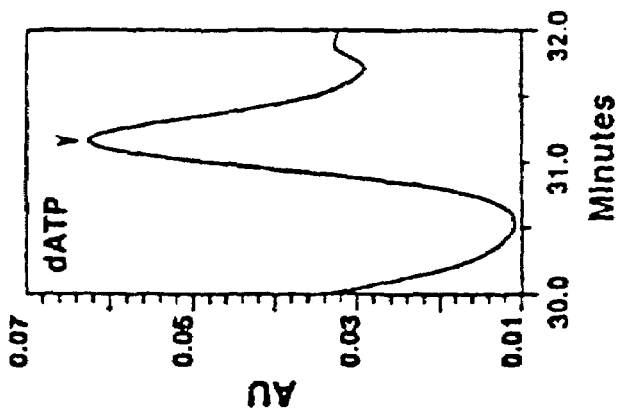
Figure 5J:
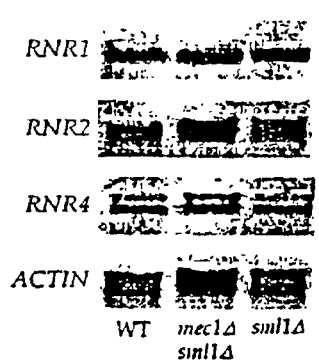
Figure 5K:
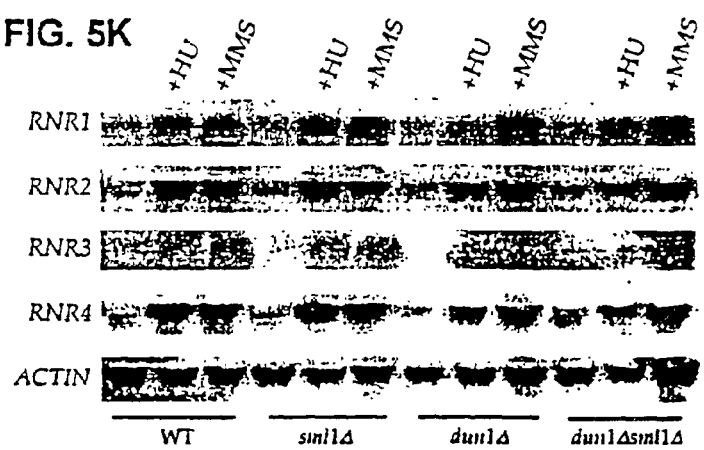

These observations are reminiscent of the effect on petite formation by different levels of RNR expression. For example, petite cells arise more frequently when RNR genes are mutated (Elledge and Davis, 1987; Wang et al., 1997a). This resembles the situation when the SML1 gene is overproduced. In addition, a mutation in the mitochondrial DNA polymerase gene, mip1-1, causes an increased frequency of petite formation that can be suppressed by overexpression of RNR1 (Lecrenier and Foury, 1995). We tested whether sml1Δ has the same effect on mip1-1 mutations, which fail to grow on non-fermentable carbon sources at 37° C. since all cells become petite (Lecrenier and Foury, 1995). As shown in FIG. 3C, sml1Δ mip1-1 cells grow well on YPGlycerol medium at 37° C., indicating that sml1Δ has the same effect as overexpression of RNR1.

Furthermore, during the course of these studies, we learned that overproduction of RNR1 can suppress the lethality of mec1 and rad53 deletions. We confirmed this result in our strain background. Thus, deletion of SML1 has the same effect on two different processes, mitochondrial replication and mec1/rad53 viability, as does overexpression of RNR1. Since RNR genes are the key regulators of dNTP synthesis (reviewed by Reichard, 1988), these observations raise the possibility that dNTP pool size may be negatively affected by SML1.

Increased Resistance to DNA Damage is Conferred by the sml1 Deletion.

To test further the hypothesis that Sml1 negatively affects dNTP levels, we examined its effect on DNA damage repair. Although an independent process from mitochondria biogenesis, DNA damage repair also requires sufficient dNTP pools, since defective alleles of the RNR genes cause DNA damage sensitivity (reviewed by Reichard, 1988; Elledge et al., 1992). Interestingly, sml1Δ strains are more resistant to HU and MMS than wild-type strains (FIG. 4A). On the other hand, duplication of the SML1 gene results in a greater sensitivity to these DNA damaging agents (FIG. 4A). These results are consistent with the hypothesis that dNTP levels are elevated in sml1Δ strains and decreased in SML1-duplication strains. However, we cannot rule out the possibility that some other step(s) of the DNA damage repair pathway(s) may also be affected leading to a similar phenotype.

To delineate which step(s) Sml1 may affect, we tested whether a sml1Δ can suppress the DNA damage sensitivity of dun1Δ strains. After DNA damage, such strains are defective in transcriptional upregulation of the RNR genes but not other DNA damage-inducible genes (Zhou and Elledge, 1993). Moreover, we found that overexpression of RNR1 in dun1Δ strains rescues UV and MMS sensitivity (data not shown), suggesting that their DNA damage sensitivity is most likely caused by lower levels of RNR activity. FIG. 4B shows that sml1Δ dun1Δ strains exhibit wild-type levels of resistance to UV (120 J/m$^2$), HU (50 mM) and MMS (0.05%). Thus, sml1Δ rescues the DNA damage sensitivity of dun1Δ strains for a broad spectrum of damage, consistent with the notion that dNTP levels are elevated in sml1 strains.

sml1Δ Strains Exhibit Increased Levels of dNTPs without Altering Transcription of the RNR Genes.

Based on the genetic evidence described above, it is likely that sml1Δ affects the size of the dNTP pools. To explore this possibility, we directly measured the dNTP levels in sml1Δ strains. Cultures of wild-type and sml1Δ strains were grown and treated in parallel (see Experimental Procedures). The levels of dNTPs were quantitated by analytical reverse phase HPLC. As shown in FIGS. 5A & 5B, the levels of dCTP, dTTP, dGTP and dATP are all increased approximately 2.5-fold in sml1Δ strains. This difference may account for the mitochondrial and DNA damage phenotype of sml1 mutants.

It is well-known that the RNR genes in *S. cerevisiae* are under transcriptional regulation. Transcription of RNR1 and RNR2 is induced at S phase and the transcription of all four RNR genes is induced after DNA damage (reviewed by Elledge et al., 1992; Wang et al., 1997a; Huang and Elledge, 1997). Thus, it is possible that the change in the size of the dNTP pools observed in sml1Δ strains is due to increased transcription. However, quantitation of the steady-state messenger RNA levels of all four RNR genes revealed no differences between wild-type, sml1Δ and mec1Δ sml1Δ strains (FIG. 5C). Furthermore, in both dun1Δ and sml1Δ dun1Δ strains, induction of RNR mRNA after HU and MMS damage is equally defective, while it is normal in sml1Δ strains (FIG. 5D). Thus, the restoration of the DNA damage response in dun1Δ strains by sml1 mutation is not due to increased transcription of RNR genes.

Interactions among Sml1, Rnr1 and Rnr2

We next tested the possibility that Sml1 interacts with the subunit(s) of RNR since such interactions may provide a regulatory mechanism to inhibit RNR activity. The yeast two-hybrid system was used and all fusion proteins, except GBD-Sml1, which shows partial complementation, were found to complement their respective defective alleles. We showed that Sml1 interacts with Rnr1 but not with Rnr2 in either orientation (Table 2). In addition, Rnr1 and Rnr2 each interacts with itself, however these interactions are much weaker than the interaction between Sml1 and Rnr1 (Table 2).

We confirmed the interaction between Sml1 and Rnr1 biochemically by co-immunoprecipitation. SML1 and RNR1 were fused to a hemagglutinin tag (HA-Sml1) and to a glutathione-S-transferase tag (GST-Rnr1), respectively. Both fusions were introduced into yeast cells under the control of GAL promoters and were able to complement their respective defective alleles. FIG. 6 shows that Sml1 and Rnr1 interact since they co-immunoprecipitate with anti-HA antibody (lane 1). Similarly, both proteins co-precipitate with glutathione beads (lane 3). This evidence confirms the two-hybrid results and supports the notion that Sml1 binds to Rnr1 in vivo.

Discussion

Here we show that a recessive suppressor sml1 can bypass the essential functions of two DNA damage and replication checkpoint genes, MEC1 and RAD53. Genetic studies also reveal that sml1 suppression does not require DUN1, TEL1 and RAD53, three genes whose overexpression can suppress mec1 lethality. One clue to the biological function of the SML1 gene product came from the observation that deletion of SML1 leads to a decreased frequency of petite formation while an extra copy causes an opposite effect (see FIG. 3). The effect of Sml1 on both cell growth and mitochondrial maintenance suggests that it may be involved in a basic biological process. One obvious candidate is the regulation of dNTP pools, since both nuclear and mitochondrial DNA syntheses in yeast use the same pools generated by de novo synthesis (reviewed by Reichard, 1988). The fact that mip1-1 strains are rescued by deletion of SML1 or by overexpression of RNR1, suggests that Sml1 may have a negative effect on dNTP pools. We tested this proposal by examining another cellular process that is also sensitive to dNTP levels, namely the DNA damage response. Interestingly, deletion of SML1 not only confers higher resistance to DNA damage but also rescues the DNA damage sensitivity of dun1Δ strains, which are defective in the induction of RNR gene transcription. Both of these observations are consistent with the idea that sml1 mutants have increased dNTP pools. Indeed, the direct measurement of the pools sizes in a sml1 mutant revealed that the levels of all four deoxyribonucleotides are higher than that observed in wild-type cells. The target for altering dNTP pool size is not at the level of RNR transcription since wild-type levels of RNR mRNA are observed in sml1 mutants both during normal growth and after DNA damage. Finally, the physical interaction between Sml1 and Rnr1, as revealed by two-hybrid and co-immunoprecipitation experiments, combined with the genetic evidence suggests a novel form of RNR regulation. We propose that the Sml1 protein modulates RNR activity by inhibiting either the formation of the RNR complex or its enzymatic activity directly.

A Model for the Regulation of RNR Activity at the Protein Level

Ribonucleotide reductase is one of the key enzymatic activities required for DNA replication and repair since it provides the dNTP pools necessary for DNA synthesis (reviewed by Reichard, 1988). As an essential participant in this process, RNR is regulated at multiple levels to achieve balance in the dNTP pools as well as to vary those pools under changing conditions. The most well-studied mechanism for regulating RNR activity is allosteric regulation, which moderates overall RNR activity as well as its substrate specificity. This regulation is achieved through effector binding at sites located in the large subunit. An unchecked imbalance in the dNTP pools can cause a decrease in the fidelity of DNA synthesis or, in extreme cases, can cause lethality via depletion of dNTP levels through allosteric inhibition (reviewed by Reichard, 1988). In addition, the activity of RNR has been reported to peak during S phase and increase after DNA damage (reviewed by Elledge et al., 1993). This fluctuation may be at least partially due to transcriptional regulation, which has been observed in both yeast and higher organisms. However, in yeast, it has not been directly demonstrated whether the change in transcription levels is coupled to a concurrent fluctuation in protein levels.

The results of the work presented here suggest an entirely new mode of RNR regulation via control of an inhibitory interaction. We propose that Sml1 binds Rnr1 to inhibit its activity when DNA synthesis is not required. During S phase or after DNA damage, a signal is transmitted to relieve the Sml1 inhibition of Rnr1. Such post-translational regulation can be achieved in the absence of protein synthesis resulting in a more rapid change in RNR activity than that afforded by transcriptional regulation. Therefore, the large subunit of RNR may be the target of three types of regulation: allosteric, transcriptional and Sml1-mediated negative control. By combining these three layers of regulation, the cell can appropriately modulate RNR activity during the cell cycle as well as rapidly respond to any external environmental changes. Consistent with its regulatory roles, the Rnr1 protein has been shown to be limiting for RNR activity in yeast extracts (Wang et al., 1997a).

What are the Essential Function(s) of Mec1 and Rad53?

In the absence of Sml1, Mec1 is no longer essential for cell viability. Based on the evidence presented here, we devise a simple model shown in FIG. 7 and propose that Mec1 functions normally to remove the inhibitory effect of Sml1 on RNR during S phase by acting on the complex. This form of regulation may also be utilized during the repair of DNA damage, which also requires increased RNR activity. The role of MEC1 in nucleotide pool regulation is consistent with the observation that overexpression of Rnr1 suppresses the lethality of mec1Δ,. The model also predicts that mec1 mutant cells have decreased dNTP pools, which may result in defective replication for both chromosomal and mitochondrial DNA. This explanation accounts for the lethality of mec1 null mutations and also for the increased frequency of petite formation exhibited in mec1-3 mutants, which is suppressed by mutation of SML1 (unpublished results). Alternatively, sml1 suppression may be indirect. For example, Mec1 may modulate the activity of some other component(s) of the DNA replication machinery, such as DNA polymerase, to increase its specificity towards dNTPs so that DNA replication occurs at a relatively low level of dNTPs. In this second model, loss of Sml1 upregulates RNR providing increased dNTP pools to make the Mec1 modulation unnecessary. We favor the first model since it ties the regulation of RNR during S phase or after DNA damage to a single pathway. On the other hand, the second model is indirect and more complicated as an additional pathway must be hypothesized to regulate the Sml1-Rnr1 interaction.

For its essential function, RAD53 is in the same pathway as MEC1 as indicated by the observation that its overexpression can suppress mec1Δ lethality (Sanchez et al., 1996). The data presented here support this hypothesis. We found that the lethality of rad53Δ is suppressed by loss of Sml1 function and that rad53 is epistatic to mec1. Moreover, overexpression of Mec1 is unable to rescue rad53 lethality further indicating that MEC1 lies upstream of RAD53.

Several lines of evidence support the notion that Mec1 and Rad53 are part of a kinase cascade that operates during the cell cycle. First, Mec1 is a protein kinase homolog (reviewed by Zakian, 1995; Bentley et al., 1996; Keegan et al., 1996). Second, the Rad53 essential function requires kinase activity, since a point mutation that abolishes this activity results in inviability (Allen et al., 1994; Fay et al., 1997). Finally, overexpression of a kinase active allele of Dun1, but not a catalytically defective allele, can rescue mec1 lethality (Sanchez et al., 1996). The Sml1/Rnr1 interaction may be a potential target of this cascade. For example, modulation of this interaction can be achieved by the phosphorylation of either Sml1 or the RNR subunits allowing the cell to rapidly regulate RNR activity during different phases of the cell cycle and/or in response to DNA damage.

Finally, the evolutionary conservation of the RNR enzymes and Mec1 homologs raises the possibility that a mechanism similar to the one described here is operating in other organisms. At first glance, this hypothesis is contradicted by the fact that ATM/Atm are not essential in mammalian cells. This difference may be due to the way dNTP synthesis occurs in yeast versus mammals. In yeast, dNTP is synthesized only via the de novo pathway employing the RNR enzyme. In mammal cells, dNTPs synthesis can also occur through a "salvage pathway," which utilizes both ribonucleosides and deoxyribonucleosides from the environment (reviewed by Reichard, 1988). In cells lacking ATM/Atm, the salvage pathway is possibly the only source for dNTPs, which may result in decreased dNTP pools and defective cell growth. This proposal is consistent with the observation that AT patients and Atm-/- mice exhibit growth retardation, which correlates with a defect in cellular proliferation and a failure to enter S phase efficiently (Barlow et al., 1996; Xu et al., 1996; Xu and Baltimore, 1996; reviewed by Shiloh, 1997). A test of this model is to measure RNR activity and dNTP pool sizes directly in these cell lines.

Experimental Procedures

Strain, Plasmids and Media

*S. cerevisiae* strains are listed in Table 3. Yeast medium were prepared essentially as described by Adams et al. (1997). HU was added to YPD medium to final concentrations ranging from 10 mM to 500 mM. MMS was added to YPD medium to final concentrations ranging from 0.005% to 0.05%. 5-fluoro-orotic acid (5-FOA) was added to synthetic complete (SC) or synthetic leucine-less medium (SC-LEU) at 750 mg/ml (Boeke et al., 1984).

Cloning of SML1

To test whether sml1-1 is dominant or recessive, diploid yeast strains homozygous for mec1-1 (mec1-1/mec1-1), heterozygous for sml1 (sml1-1/SML1) and containing MEC1 on a plasmid (pRS416-MEC1, a CEN-MEC1-URA3 plasmid) were generated as follows. Several mec1-1 {pRS416-MEC1} strains, which were characterized by their inability to grow on SC 5-FOA medium, were obtained after dissecting mec1-1/MEC1 sml1-1/SML1 heterozygous diploids that contained this plasmid. They were next mated with mec1-1 sml1-1 strains. Cells from these diploids fail to grow on SC 5-FOA medium since they cannot lose the MEC1-containing plasmid indicating that sml1-1 is recessive.

To clone SML1, we used the red/white sectored colony assay described in the text (Koshland, 1985). The indicator strain U940 contains plasmid pC87 (CEN-ADE3-MEC1-URA3). A CEN-LEU2 plasmid-based genomic library was used. Four solid red color colonies were recovered and streak-purified on SC-LEU 5-FOA medium as a secondary screen to eliminate false positives. Plasmids from the two colonies that failed to grow on SC-LEU 5-FOA plates were recovered and one was named pWJ739.

Restriction enzyme digestion and DNA sequence analysis of the ends of the insert revealed that pWJ739 contains a DNA sequence encompassing ORFs YML059C, YML058W and most of the CMP2 gene of chromosome XIII (Cherry et al., 1997). Three deletion plasmids were constructed and tested for their ability to complement sml1-1 (FIG. 1B). In plasmid pWJ661, a 6.7 kb HindIII-SacII fragment is deleted to remove YML059C. In pWJ664, a 1.6 kb SnaBI-PmlI fragment is further deleted so that both YML059C and CMP2 are removed. In pWJ66S, a 1.6 kb NcoI-NcoI fragment is deleted from pWJ661 so that YML085W is also removed.

A 1.7 kb SphI-SalI fragment containing SML1 and part of CMP2 was cloned into YIp5 (Struhl et al., 1979) to construct pWJ660. pWJ660 was linearized at its SpeI restriction site and transformed into a wild type strain. Homologous insertion of this fragment into the SML1 locus marks it with URA3 and simultaneously causes a duplication of SML1. The resulting strain (U946) was crossed to a mec1-1 sml1-1 strain and no URA3 mec1-1 spores were recovered from 54 tetrads dissected.

Genetic Analyses

To follow the sml1-1 allele in genetic crosses, yeast colony PCR reactions were carried out (Adams et al., 1997). Using primer pair A (SEQ ID NO:3) and C (SEQ ID NO: 4) (Table 4), the wild-type and the sml1-1 alleles give rise to 570 bp and 280 bp PCR products, respectively.

To test whether overproduction of Mec1 rescues rad53 lethality, a GAL-MEC1 plasmid (pWJ701) was constructed. The native promoter of MEC1 on pRS416-MEC1 was replaced with a GAL1-10 promoter fragment (generated from a PCR reaction using primer pair p416-GAL 5' (SEQ ID NO: 9) and MEC1-GAL 3' (SEQ ID NO: 10), Table 4) through in vivo DNA recombination (Ma et al., 1987). This plasmid was then transformed into rad53Δ/RAD53 sml1-1/SML1 heterozygous diploids. After dissection of 66 total tetrads from six different transformants, no rad53Δ {pGAL-MEC1} spores were recovered on galactose-inducing medium. However, in the same dissections, the pRS416-MEC1 plasmid segregated into RAD53 or rad53 sml1 spores normally. Moreover, in a separate experiment, rad53Δ strains cannot lose a CEN-RAD53 plasmid (pWJ676) even when MEC1 is overexpressed.

All SML1 constructs were tested for functional complementation using the same red/white sector system described above for identifying the SML1 clone. Partial complementation is designated when small white sectors were observed.

Gene Disruptions

Gene disruptions for SML1 and DUN1 were performed as described by Baudin et al. (1993). Forty-five base pairs of homology adjacent to each ORF was added to HIS3 and URA3 selectable markers, respectively, by PCR with the primers listed in Table 4 (SML1-HIS3 5' (SEQ ID NO: 5) & SML1-HIS3 3' (SEQ ID NO: 6) and dun1d 5' (SEQ ID NO: 7) & dun1d 3' (SEQ ID NO: 8)). MEC1 was disrupted in diploids using a fragment that contains the 800 bp TRP1 marker (from pUC18-TRP1) replacing the sequence from 98 bp to 7764 bp (BamHI-SacII) of the MEC1 ORF (Rothstein, 1983). RAD53 was disrupted by transforming the EcoRI fragment containing rad53Δ::HIS3 (Zheng et al., 1993). All disruptions were confirmed by genomic blots and genetic analysis.

Measurement of the Frequency of Petite Formation

Strains were streaked on YPGlycerol plates to eliminate petite cells. Single colonies were next inoculated into YPD liquid medium at a starting concentration of $1.4 \times 10^5$ cells/ml and cultured for approximately 7 generations. Appropriate dilutions of cells were plated on YPD plates and incubated at 30° C. for three days. The frequency of petite formation was calculated after replicating to YPGlycerol medium. At least five independent strains for each genotype were analyzed and 1000–2000 colonies were plated for each trial. The mean frequency and standard deviation were calculated and plotted in FIG. 3B. The differences in the frequency of petite formation between wild type and sml1Δ, or wild type and SML1-duplication strains are statistically significant (P=0.0023 and 0.001, respectively).

Measurement of UV, HU and MMS Sensitivity

Mid-log phase cultures were sonicated and counted. Tenfold dilutions from $10^5$–10 cells were spotted on YPD plates and on YPD plates containing HU (10 mM–500 mM) or MMS (0.005%–0.1%). One set of YPD plates was irradiated by UV light at 120 J/m$^2$. Plates were next incubated at 30° C. for three days. For each genotype tested, at least two independent strains were assayed twice.

Measurement of Deoxyribonucleotides

Procedures for the extraction and purification of deoxyribonucleotides were based on the protocols of Muller, E. G. D. (Muller, 1994) except for the following changes. Cultures were harvested by rapid filtration onto a 47 mm GH Polypro membranes (0.45 μM, Gelman Sciences). Only the first 7 fractions of the deoxyribonucleotide peak off of the boronate column (0.7×13.5) were collected. Based on the chromatography of standards, these 7 fractions contained 90% of the deoxyribonucleotides and >90% of the ribonucleotides were removed.

Separation of the deoxyribonucleotides was performed by reversed phase HPLC. HPLC was performed with a Waters 717 plus autosampler at 4° C., a Symmetry C18 (4.6×250 mm) column and the 996 photodiode array detector. Automation and data analysis was done with the Waters Millennium software. The preparation of buffers and run conditions were as described (Cross et al., 1993). The photodiode array detector collected data from 230 nm to 300 nm at a rate of 1 spectrum/sec and a resolution of 3.6 nm. The elution profile was monitored at 254 nm.

The extracts were resolved into 45 peaks with elution times from 3.6 to 46 min. The identification of the DATP, dCTP, dTTP and dGTP peaks in the samples were established by three criteria: 1) a 230–300 nm spectrum that matched standards, 2) an elution time that was within 0–4% of the standards and 3) the coelution of the peak with standards that were added to the sample. Calibration curves were created using the Millennium software with peak areas. Standards at 100 mM were supplied from BOEHRINGER MANNHEIM®.

RNA Analysis

Cultures were grown in YPD liquid to $OD_{600}$=0.5 at 30° C. Total RNA was prepared, separated on a formaldehyde 1.5% agarose gel and blotted to Hybond™-N+ membrane according to the directions of the manufacturer (Amersham). The RNA blots were probed sequentially with $^{32}$P-labeled 800 bp HindIII fragment of RNR1 (from plasmid pSE738; Elledge and Davis, 1989), 900 bp HindIII fragment of RNR2 (from plasmid pSE310; Elledge and Davis, 1987), 1.1 kb BamHI-EcoRI fragment of RNR3 (from plasmid pSE734; Elledge and Davis, 1989), a 1.2 kb PCR fragment of the RNR4 ORF or a 500 bp EcoRI-HindIII actin fragment. The actin probe was used as an RNA loading control. Cells were exposed to the DNA damaging agents HU (150 mM) and MMS (0.015%) for 3 hours before extraction as described above.

Two-hybrid Assay

The strains and plasmids for two-hybrid analysis were PJ69-4A, pGBD-C2, pGAD-C2 (James et al., 1996) and pACTII (CLONTECH® Inc.). The primer pair pB-SML1 5' (SEQ ID NO: 11) and pGBD-SML1 3' (SEQ ID NO: 13) (Table 4) was used to amplify the SML1 ORF. After digestion with BamHI and PstI, this PCR product was cloned into the BamHI-PstI sites of pGBD-C2 to construct plasmid pWJ728. Similarly, plasmid pWJ684 contains a BamHI fragment from the PCR product of the SML1 ORF generated using the primer pair pB-SML1 5' and pB-SML1 3' (SEQ ID NO: 12) (Table 4) and inserted at the BamHI site of pACTII. PCR fragments containing the RNR1 or the RNR2 ORF were generated by primer pairs RNR1-ORF 5' (SEQ ID NO: 14) and RNR1 3' (SEQ ID NO: 15) or RNR2-ORF 5' (SEQ ID NO: 17) and RNR2 3' (SEQ ID NO: 16) (Table 4). These fragments were cloned into the BamHI-PstI site of pGBD-C2 and pGAD-C2 to construct pWJ731 and pWJ745 or pWJ729 and pWJ746 respectively.

The GAL1-HIS3 reporter was assayed on SC-HIS-LEU-TRP medium plus 1-2 mM 3-aminotriazole. The GAL2-ADE2 reporter was assayed on SC-ADE-LEU-TRP medium. Weaker interactions (recorded as +/− in Table 2) do not permit growth on this medium, however they can give rise to white/red sectored colonies on YPD medium.

Co-immunoprecipitation and Western Blot Analysis

The GST-Rnr1 fusion plasmid, pWJ744, was generated by inserting a BamHI-SalI fragment from the PCR product of the RNR1 ORF generated using primers RNR1-5'+0 (SEQ ID NO: 18) and RNR1 3' far (SEQ ID NO: 19) into the BamHI-SalI sites of pEG(KT) (Mitchell et al., 1993). The SML1 ORF was amplified using primer pYX-SML1 5' (SEQ ID NO: 20) and pB-SML1 3' and the BamHI-digested PCR product was cloned into BamHI site of pYX423. Next, an EcoRI fragment of a 3XHA tag (Schneider et al., 1995) generated after PCR using primer pair HA 5' (SEQ ID NO: 21) and HA 3' (SEQ ID NO: 22) was added to the N-terminus of SML1 to construct plasmid pWJ699. Both pWJ744 and pWJ699 can functionally complement rnr1 and sml1, respectively.

Transformants containing these two plasmids were grown to $OD_{600}$=0.25 in SC-LEU-URA medium with 2% raffinose replacing glucose. Two percent galactose was added and the cultures were grown for 5 more hours. Next, protein extracts were prepared by the glass bead disruption method in NP-40 buffer (150 mM NaCl, 1% NP-40, 50 mM Tris (pH 8.0), 2 μM pepstatin A, 2 mM benzamidine, 1 mM EDTA, 100 μM leupeptin, 19 μg/ml aprotinin, 1 mM PMSF, 5 μg/ml chymostatin; Harlow and Lane, 1988). Protein concentration was measured using the Bio-Rad Protein Assay. Five hundred μg of protein extract was incubated with either 200 μl of a 50% slurry of glutathione beads for 30 min. or 1 μg anti-HA antibody (3F10, BOEHRINGER MANNHEIM®) for 1 hour followed by incubation with 50 μl of 50% protein G beads for 3 hours. All incubations were carried out at 4° C. After washing 5 times with NP-40 buffer, protein complexes were dissolved in 100 μl SDS gel loading buffer and were separated on a 7.5% gel and a 15% PAGE gel. The proteins were transferred to nitrocellulose and anti-GST antibody (MOLECULAR PROBES®) and anti-HA antibody (3F10) were used to detect GST-Rnr1 and HA-Sml1, respectively.

EXAMPLE 6

Yeast Sml1, a Protein Inhibitor of Ribonucleotide Reductase

The following is an example that biochemically demonstrates that Sml1 functions as a strong protein inhibitor of ribonucleotide reductase (RNR) activity. This confirms our results with this protein. The example shows that Sml1 binds to and decreases the activity of a mammalian RNR. These results strengthen the case for using Sml1 peptide mimetics to help develop potential drugs to target RNR.

Ribonucleotide reductase (RNR) catalyzes the reduction of ribonucleotides to deoxyribonucleotides; this step is rate limiting in DNA precursor synthesis. A number of regulatory mechanisms ensure optimal deoxyribonucleotide pools, which are essential for cell viability. The best studied mechanisms are transcriptional regulation of the RNR genes during the cell cycle and in the response to DNA damage, and the allosteric regulation of ribonucleotide reductase by nucleoside triphosphates. Recently, another mode of RNR regulation has been hypothesized in yeast. A novel protein, Sml1, was shown to bind to the Rnr1 protein of the yeast ribonucleotide reductase; this interaction was proposed to inhibit ribonucleotide reductase activity when DNA synthesis is not required (Zhao, X., Muller, E. G. D., and Rothstein, R. (1998), *Mol. Cell* 2, 329–340). Here, we use highly purified recombinant proteins to directly demonstrate that the Sml1 protein is a strong inhibitor of yeast RNR. The Sml1 p specifically binds to the yeast Rnr1p in a 1:1 ratio with a dissociation constant of 0.4 μM. Interestingly, Sml1p also specifically binds to the mouse ribonucleotide reductase R1 protein. However, the inhibition observed in an in vitro mouse ribonucleotide reductase assay is less pronounced than the inhibition in yeast and probably occurs via a different mechanism.

Ribonucleotide reductase (RNR)[1] plays a crucial role in DNA synthesis, by catalyzing the direct reduction of all four ribonucleotides to deoxyribonucleotides. Both the yeast and mammalian ribonucleotide reductases belong to the ribonucleotide reductase class Ia; in this class, the active enzymes consist of a large subunit and a small one (1). In mammalian cells, these two non-identical homodimeric subunits are encoded by the R1 and R2 genes, respectively. The R1 protein contains redox active dithiols, the active site binding nucleoside diphosphate substrates and binding sites for nucleoside triphosphates that act as allosteric effectors. Substrate specificity is controlled by binding of ATP, dATP, dTTP or dGTP to a specificity site, while overall activity is controlled by binding of ATP (active) or dATP (inactive) to an activity site (2). Failure to control the size of dNTP pools and/or their relative amounts leads to cell death or genetic abnormalities (3).

[1] The abbreviations used are: RNR, ribonucleotide reductase; RU, resonance unit The R2 protein contributes a tyrosyl free radical, which is essential for RNR activity; this radical is generated by a binuclear iron center (2). The flexible C-terminal tail of the R2 polypeptide chain is essential for the R1 and R2 interaction, and upon binding to the R1 protein, the flexible R2 protein tail becomes rigid (4). Peptides and peptidomimetics corresponding to the R2 protein C-terminal inhibit ribonucleotide reductase in a species specific way (5).

In *S. cerevisiae*, there are two genes encoding R1-like proteins, RNR1 and RNR3 (6); there are also two genes encoding R2-like proteins, RNR2 (7,8) and RNR4 (9,10). The yeast ribonucleotide reductase genes are one of the targets of the Mec1-Rad53 dependent DNA damage/cell cycle checkpoint pathway (11). Overexpression of the yeast RNR genes suppresses the lethality of strains lacking Mec1 or Rad53, supposedly by increasing the dNTP pools (12). Unlike the mammalian enzyme, the yeast RNR is not inhibited by physiological concentrations of dATP; this observation explains the positive correlation between enzyme and dNTP levels in yeast[2]. Recently, Zhao et al. (13) identified a novel protein that negatively affects dNTP pools in yeast, and they called it Sml1p. Deletion of SML1 rescued the lethality of a mec1 or rad53 strain. Sml1p was shown to interact with the yeast Rnr1 protein using the two-hybrid system and co-immunoprecipitations. For this reason, a novel mode of RNR regulation was suggested, where Sml1p binding to the Rnr1 protein would inhibit the enzyme.

[2] A. Chabes and L. Thelander, submitted for publication.

Using highly purified recombinant proteins, we now directly demonstrate in an in vitro yeast ribonucleotide reductase assay that Sml1p is indeed a very potent inhibitor of yeast RNR. It specifically binds to the yeast Rnr1p as shown by biosensor technique using sensor chips with immobilized Sml1p. Interestingly, the Sml1p also specifically binds to the mouse R1 protein with high affinity. However, the inhibition seen in an in vitro mouse ribonucleotide reductase assay is less pronounced than in the yeast system, which indicates an inhibition mechanism different from the one in yeast. These findings may be used to develop a new generation of antiproliferative drugs targeted to RNR.

Materials and Methods

Recombinant proteins and peptides. The recombinant yeast proteins Rnr1, Rnr2 and Rnr4 were expressed in *E. coli* BL21 (DE3) bacteria using the pET3a expression vector; mouse recombinant proteins R1 and R2 were expressed in *E. coli* BL21 (DE3)pLysS bacteria using the same vector (14). Purification of the recombinant mouse and yeast R1 proteins, and of the recombinant mouse R2 protein, was made as described earlier (15,16). The yeast Rnr2 and Rnr4 proteins were coexpressed and purified as a heterodimer[3]. The SML1 coding sequence (13) was amplified by PCR from yeast genomic DNA using the following oligonucleotides: 5'-CAA TAA TTT CCC CAT ATG CAA AAT TCC-3' (SEQ ID NO: 23) and 5'-AAA GGA TCC TTA GAA GTC CAT TTC CTC GAC-3' (SEQ ID NO: 24). After the PCR product was cleaved with NdeI and BamHI restriction endonucleases, it was cloned into the pET3a vector digested with the same restriction enzymes. The SML1 sequence in the resulting plasmid was checked by DNA sequencing. Recombinant yeast Sml1p was expressed in *E. coli* BL21 (DE3)pLysS bacteria by growing a culture at 37° C. to an OD of 0.6 at 600 nm, followed by induction with 0.5 mM IPTG. After 3 hours, the bacteria were harvested by centrifugation, resuspended in 50 mM Tris-HCl, pH 7.4, 1 mM EDTA, and lysed by freezing in liquid nitrogen. After thawing, the lysate was centrifuged at 150000×g, 4° C. for 1 h. Proteins in the supernatant were precipitated by adding solid ammonium sulfate to 25% saturation at 0° C. (0.136 g/ml). The pellet was dissolved in the same buffer as above; finally, the solution was centrifuged through Ultrafree-MC Millipore 30,000 NMWL Filter units with a 30 KDa cut-off value to obtain pure Sml1 protein in the filtrate.

[3] V. Domkin, A. Chabes and L. Thelander, manuscript in preparation.

N-acetylated peptides corresponding to the last 9 amino acids of either Rnr2p (GAFTFNEDF) (SEQ ID NO: 25), Rnr4p (KEINFDDDF) (SEQ ID NO: 26) or Sml1p (QGKVEEMDF) (SEQ ID NO: 27) were ordered from Genosys.

Protein concentrations. Protein concentrations were determined by reading the absorbance at 280 nm, and using the earlier published $E^{1\%}_{1\,cm}$ of 12 (mouse R1 and yeast Rnr1 proteins (15)) or 13.7 (mouse R2 protein (16)). The corresponding value for the Rnr2p/Rnr4p heterodimer (12.9) was obtained from quantitative amino acid hydrolysis of aliquots from solutions with known absorbance. The concentration of Sml1p solutions was determined using an $E^{1\%}_{1\,cm}$ of 7.1 based on calculations (DNA star, Inc.) from the amino acid composition.

BIAcore biosensor analysis. The interaction between Sml1p and either yeast Rnr1p or mouse R1 protein was studied by biosensor analysis using the BIAcore method (Biacore AB). The Sml1 protein was prepared in 10 mM sodium acetate, pH 5.2, at a concentration of 0.44 mg/ml; it was then immobilized on the dextran layer of the sensor chip as described previously for the mouse R2 protein (17). The ligand proteins were equilibrated with running buffer (10 mM Hepes-KOH, pH 7.4, 200 mM potassium acetate, 1 mM EDTA, 5 mM magnesium acetate and 0.05% Surfactant P20 (BIAcore). The interactions were studied at a constant temperature of 22° C. and a constant flow of 5 μl/min. Kinetics for the interaction of Sml1p with yeast Rnr1p was determined by allowing the immobilized Sml1p to interact with increasing concentrations of Rnr1p (18). The resonance unit (RU) is proportional to the mass, and 1 RU corresponds to a surface concentration of 1 pg of protein/mm² of the 100 nm thick dextran layer (19).

Sucrose gradient centrifugation. Rnr1p (500 μg) was incubated in 0.1 ml of 20 mM Hepes-KOH, pH 7.4, 100 mM potassium acetate, 10 mM magnesium acetate, 5 mM dithiothreitol, and 0.1 mM dTTP if indicated, in the presence or absence of 90 μg of Sml1 protein. After 30 min incubation at 25° C., the samples were cooled on ice and mixed with 0.75 μg of bovine liver catalase (Sigma); catalase served as a marker for the determination of sedimentation coefficients. The 0.1 ml samples were layered onto 4.0 ml of a 5 to 20% linear gradient of sucrose in the same buffer as above, and centrifuged for 14 h at 40,000 rpm in a Beckman SW 60 rotor at 4° C. The bottom of each tube was punctured, and fractions of approximately 0.1 ml were collected. Aliquots of each fraction were removed for spectrophotometric assay of catalase activity (20); protein concentration as determined by the Bradford method (21); or SDS-PAGE analysis.

Results

Purification of recombinant yeast Sml1 protein. As seen in FIG. 8, pure recombinant Sml1 protein was obtained after only three purification steps—ultracentrifugation, ammonium sulfate fractionation and ultrafiltration. The yield was about one mg of pure protein per liter of bacterial culture.

Inhibition of yeast ribonucleotide reductase by the Sml1 protein. Recombinant yeast ribonucleotide reductase was assayed for activity using a CDP reduction assay, with ATP as a positive effector in the presence of increasing amounts of Sml1 protein (FIG. 9). A molar ratio of 1:1 between Rnr1p monomer (MW 100000) and Sml1p (MW 11800) gave about 50% inhibition. The amounts of Rnr2p/Rnr4p heterodimer were varied (1 to 32 μg) at one fixed amount of Rnr1p (2 μg) and 0, 0.2 and 2 μg of Sml1p; this experiment did not give any evidence of competition between Sml1p and the Rnr2p/Rnr4p heterodimer for binding to Rnr1p. Instead the data fitted best to a noncompetitive inhibition (data not shown).

Inhibition of yeast ribonucleotide reductase by nonapeptides corresponding to the C-terminal ends of Sml1p, Rnr2p or Rnr4p. The C-terminal sequence of the Sml1p shows some homology to the C terminal peptides of the Rnr2 or Rnr4 proteins. Since such peptides are known to inhibit RNR activity by binding to the R1 protein and preventing R1/R2 interaction, we wanted to study the influence of a C-terminal nonapeptide of Sml1p on yeast RNR activity. As shown in FIG. 10, nonapeptides from the C terminus of Rnr2p or Rnr4p inhibited the in vitro yeast RNR assay to about the same extent with an IC$_{50}$ of 44 and 30 µM, respectively. In contrast, the nonapeptide corresponding to the C terminus of Sml1p showed an inhibition with an IC$_{50}$ of only about 300 µM.

Interaction between yeast Rnr1 protein and Sml1 protein assayed by sucrose gradient centrifugation. For enzymatic activity, ribonucleotide reductases of the class Ia type must form a heterodimeric complex composed of homodimeric R1 and R2 proteins. It was previously demonstrated for the mouse RNR that binding of effectors to the substrate specificity site promotes formation of the R1 dimer, which is believed to be a prerequisite for binding to the R2 dimer (18,23). To test if Sml1p binding to the Rnr1p might interfere with Rnr1p dimer formation and thereby inhibit RNR activity, we preincubated Rnr1p and Sml1p in the presence of the allosteric effector dTTP; we then analyzed the mixture on a sucrose gradient (FIG. 11). The addition of dTTP induced formation of dimers and tetramers of the Rnr1p and no monomer peak could be seen in the gradient. This pattern is quite different from the one shown in the absence of dTTP, where the Rnr1p monomers dominate (FIG. 11). Addition of Sml1p did not influence the distribution of Rnr1p in the gradient, and no shift from dimers to monomers could be observed. At the same time, analysis of the fractions by SDS-PAGE clearly demonstrated two peaks of Sml1p, one minor peak cosedimenting with the dimer peak of Rnr1p and one major peak representing free Sml1p sedimenting at the top of the gradient. The fact that a portion of Sml1 protein was present in the fractions containing the Rnr1p dimers indicates that the Sml1p can bind to the Rnr1p dimer without dissociating it into monomers. No shift towards Rnr1p monomers was observed under the following conditions: the Rnr1p/Sml1p/dTTP incubation mixture was sedimented through a gradient containing Sml1p at a concentration of 0.15 mg/ml throughout to minimize Rnr1p-Sml1p dissociation (data not shown). Therefore, binding of Sml1p did not influence the monomer/dimer equilibrium of the Rnr1p.

Kinetic studies of the interaction between the Rnr1 and Sml1 proteins using a biosensor technique. To obtain a quantitative description of the Rnr1p and Sml1p interaction, we immobilized the Sml1 protein to the dextran layer of a sensor chip, and then injected a series of solutions containing increasing concentrations of Rnr1p to the same sensor chip. The immobilization of Sml1p at a concentration of 0.44 mg/ml gave an increase of 91 resonance units (RU), which correspond to 91 pg/mm$^2$. With a surface of 0.8 mm 2, 91 RU corresponds to a total of 72.8 pg of bound Sml1p, which can be compared with the total injected amount of 15.4 µg. This low degree of attachment (only 0.0005%) makes it unlikely that the protein is attached to multiple binding sites.

Increasing concentrations of Rnr1p resulted in increasing equilibrium values, which approached a maximal value (FIG. 12A). In control experiments, where the same series of Rnr1p solutions passed a sensor chip without immobilized Sml1p, a "bulk effect" gave a response of only about 60 RU. The same background value of about 60 RU was observed when bovine serum albumin or Rnr2p/Rnr4p heterodimer was injected at a concentration of 0.1 mg/ml (data not shown). In FIG. 1B, the response at equilibrium is plotted against the concentration of injected Rnr1p. Using the GraphPad Prism program (GraphPad Software, Inc.), an equilibrium dissociation constant (KD) of 0.41±0.1 µM and a maximal binding of 691 RU were obtained. These values correspond to 691 pg/mm$^2$ or a total of 553 pg or 5.5 fmol Rnr1p monomer bound to about 6.2 fmol immobilized Sml1p, i.e. nearly one Rnr1p monomer bound per molecule of immobilized Sml1p. Using the BIAevaluation software (Biacore AB), an association rate constant of about 153000 M$^1$s$^{-1}$ and a dissociation rate constant of 0.04 s$^{-1}$ were obtained from the lower curves in FIG. 12A. Calculating the equilibrium dissociation constant from these rate constants gave a K$_0$ of about 0.25 µM, which is close to the directly determined K$_0$. Mixing the Rnr1p with Rnr2p/Rnr4p heterodimer, with or without dTTP before injection, did not affect the curves; the same results were obtained as when Rnr1p was injected alone.

Inhibition of mouse ribonucleotide reductase by the Sml1 protein. The effects of Sml1 protein on pure recombinant mouse ribonucleotide reductase were tested in a CDP assay in the presence of ATP as a positive effector (FIG. 13). In the figure, RNR activity in the presence of a fixed amount of R1 protein, and in the presence or absence of a 300 fold molar excess of Sml1p, are plotted against increasing concentrations of the R2 protein. In contrast to the situation with the yeast RNR, this inhibition is less pronounced and dependent on the R1 to R2 ratio. In a double reciprocal plot, clear competition is observed between Sml1p and the R2 protein (data not shown).

Kinetic studies of the interaction between the mouse RNR R1 protein and the Sml1 protein using a biosensor technique. After observing inhibition of the mouse RNR by Sml1p, we wanted to characterize the binding between the mouse R1 protein and Sml1p. As before, the Sml1p was immobilized on a sensor chip, and a solution containing 0.1 mg/ml of mouse R1 protein was injected (FIG. 14). On injection, a very rapid association phase was observed; this phase was immediately followed by a prolonged dissociation phase that never reached an equilibrium plateau. Injecting the R1 solution over an empty sensor chip gave the same low background value as observed earlier. Injection of mouse R2 protein also resulted in only background values (data not shown). To exclude the possibility that the unexpected behavior of the mouse R1 protein was due to improperly immobilized Sml1p, we injected 0.1 mg/ml of the yeast Rnr1 protein; we observed the same type of response as in FIG. 12A, with a clear equilibrium plateau. Knowing that allosteric effectors affect the conformation of R1 proteins, we next mixed the mouse R1 protein with dTTP before injection. This time, a rapid association phase was followed by a clear equilibrium plateau; this sensorgram resembled the sensorgram obtained with the yeast Rnr1p. Finally, we mixed the mouse R1 protein plus dTTP with R2 protein before injection, expecting to see an R1/R2 complex bound to Sml1p. However, the R2 protein addition almost abolished the specific R1 binding, and resulted in almost background values. No attempts were made to quantify the mouse R1 binding data, since the sensorgrams deviated widely from standard curves.

Discussion.

Our in vitro data directly prove the hypothesis of Zhao et al. (13) that the yeast Sml1 protein is a physiological inhibitor of ribonucleotide reductase; this is a new concept in the RNR field. So far, no mammalian homologue has been identified, and no homologous proteins could be found in available databases. This situation may reflect different control of ribonucleotide reductase activity in yeast and mammalian cells. In yeast, transcriptional activation of the RNR genes and suppression of the Sml1 protein lead to increased RNR activity and deoxyribonucleotide pools after DNA damage (12, 13). In contrast, mammalian cells control RNR activity by an S-phase/DNA-damage specific stabilization of the R2 protein, until cells enter into mitosis, in combination with negative feedback regulation by dATP$^2$. We suggest that the Sml1 protein may substitute for DATP feedback regulation, since yeast RNR is not inhibited by physiological concentrations of DATP. Therefore, unlike in mammalian cells, there is a direct correlation between levels of RNR proteins and deoxyribonucleotide pools in yeast cells.

The Sml1 protein specifically binds to the yeast Rnr1 protein with a dissociation constant of 0.4 µM and in a 1:1 ratio at saturation. Binding did not influence the R1 monomer/dimer equilibrium, and no competition with the R2/R4 heterodimer was observed. These observations may indicate separate binding areas on the R1 protein, or that the affinity of the Rnr1p/Sml1p interaction is much higher compared to the Rnr1p interaction with the R2/R4 heterodimer. For mouse and E. coli RNRs, the dissociation constant for the R1/R2 complex was reported to be around 0.1 µM (18); the subunit interaction in the yeast RNR appears much weaker, however, and we have not yet been able to quantify it. On a molar basis, the Sml1 protein is about 200 times more efficient in inhibiting yeast RNR activity than its C terminal nonapeptide. Furthermore, unlike Sml1p inhibition, peptide inhibition depends on the concentration of the R2/R4 heterodimer.

The yeast Rnr1 protein and the mouse R1 protein show 68% amino acid sequence identity, and the sequence similarities are distributed along the whole polypeptide chain. Still, it was quite unexpected that the Sml1 protein would also specifically bind to the mouse R1 protein. However, as indicated by the sensorgram that shows mouse R1 binding to Sml1p, the initial rapid binding was followed by a prolonged dissociation that is prevented by the addition of dTTP. This finding may indicate conformational changes induced by dTTP that makes the R1 protein a better target, or that binding of the R1 dimer is preferred. Furthermore, both in the mouse RNR assay and in the biosensor experiments, clear competition was observed between Sml1p and the mouse R2 protein for binding to the R1 protein. Therefore, the inhibition mechanism may differ for yeast and mouse RNR enzymes. While inhibition in the yeast system is very efficient and may involve blocking the entrance to the active site, inhibition in the mouse system is rather inefficient and may reflect blocking R2 protein binding to the R1 protein, perhaps in the same way as R2 protein C terminal peptides.

The structural studies of the Sml1 protein, alone and bound to the R1 protein, will reveal the mechanism of inhibition. This finding should be useful in developing specific antiproliferative inhibitors of RNR; such new inhibitors could complement existing ones, which include radical scavengers, iron chelators and peptidomimetics (2).

REFERENCES

1. Reichard, P. (1993) *Science* 260, 1773–1777.
2. Thelander, L., and Gräslund, A. (1994) in *Metal Ions In Biological Systems*, eds. Sigel, H., and Sigel, A. (Marcel Dekker, New York), 109–129.
3. Reichard, P. (1988) *Annu. Rev. Biochem.* 57, 349–374.
4. Lycksell, P. C., Ingemarson, R., Davis, R., Graslund, A., and Thelander, L. (1994) *Biochemistry* 33, 2838–2842.
5. Liuzzi, M., Deziel, R., Moss, N., Beaulieu, P., Bonneau, A. M., Bousquet, C., Chafouleas, J. G., Garneau, M., Jaramillo, J., Krogsrud, R. L., and et al. (1994) *Nature* 15, 695–698
6. Elledge, S. J., and Davis, R. W. (1990) *Genes. Dev.* 4, 740–751
7. Elledge, S. J., and Davis, R. W. (1987) *Mol. Cell. Biol.* 7, 2783–2793
8. Hurd, H. K., Roberts, C. W., and Roberts. J. W. (1987) *Mol. Cell. Biol.* 7, 3673–3677
9. Wang. P. J., Chabes. A., Casagrande. R., Tian. X. C., Thelander. L., and Huffaker. T. C. (1997) *Mol. Cell. Biol.* 17, 6114–6121
10. Huang. M., and Elledge. S. J. (1997) *Mol. Cell. Biol.* 17, 6105–6113
11. Weinert, T. (1998) *Cell* 94, 555–558
12. Desany, B. A., Alcasabas. A. A., Bachant, J. B., and Elledge, S. J. (1998) *Genes. Dev.* 12, 2956–2970
13. Zhao, X., Muller, E. G., and Rothstein, R. (1998) *Mol. Cell.* 2, 329–340
14. Studier, F. W., Rosenberg, A. H., Dunn, J. J., and Dubendorff, J. W. (1990) *Methods. Enzymol.* 185, 60–89
15. Davis, R., Thelander, M., Mann, G. J., Behravan, G., Soucy, F., Beaulieu, P., Lavallee, P., Gräslund, A., and Thelander, L. (1994) *J. Biol. Chem.* 269, 23171–23176
16. Mann, G. J., Gräslund, A., Ochiai, E., Ingemarson, R., and Thelander, L. (1991) *Biochemistry* 30, 1939–1947
17. Rova, U., Goodtzova, K., Ingemarson, R., Behravan, G., Gräslund, A., and Thelander, L. (1995) *Biochemistry* 34, 4267–4275
18. Ingemarson, R., and Thelander, L. (1996) *Biochemistry* 35, 8603–8609
19. Jönsson, U., Fägerstam, L., Ivarsson, B., Johnsson, B., Karlsson, R., Lundh, K., Lofas, S., Persson, B., Roos, H., Ronnberg, I., and et al. (1991) *Biotechniques* 11, 620–627
20. Chance, B., and Herbert, D. (1950) *Biochem. J.* 46, 402
21. Bradford, M. M. (1976) *Anal. Biochem.* 72, 248–254
22. Engström, Y., Eriksson, S., Thelander, L., and Åkerman, M. (1979) *Biochemistry* 18, 2941–2948
23. Thelander, L., Eriksson, S., and Åkerman, M. (1980) *J. Biol. Chem.* 255, 7426–7432

Footnotes:

This work was supported by the Swedish Natural Sciences Research Council, the Medical Faculty of Umeå University, and by fellowships to V. Domkin from the foundation Wenner-Grenska Samfundet and The Royal Swedish Academy of Sciences.

TABLE 1

Genetic Analysis Reveals a Second Locus Suppressor of mec1-1 Lethality

| Strains | mec1-1 segregants (alive:dead) | MEC1 segregants (alive:dead) |
|---|---|---|
| mec1-1 X MEC1 in W303 | 155:149 | 293:11 |
| mec1-1 X MEC1 in SK1 (AMP107) | 19:25 | 39:5 |
| mec1-1 X MEC1 in S288C (MCY3647) | 19:25 | 42:2 |
| mec1-1 X MEC1 in A364a (YCH13) | 22:22 | 41:3 |
| mec1-1 sml1-1 X MEC1 sml1-1 | 143:9 | 147:5 |

Only relevant genotypes of strains are listed. The mec1-1 strain is DLY258. The MEC1 sml1-1 strain was chosen from a tetrad with two viable spores. MEC1 and mec1-1 were scored by UV sensitivity.

TABLE 2

Two-Hybrid Interactions

| GBD fusion | GAD-SML1 | | | GAD-RNR1 | | | GAD-RNR2 | | | GAD | | |
|---|---|---|---|---|---|---|---|---|---|---|---|---|
| | HIS3 | ADE2 | LacZ | HIS3 | ADE2 | LacZ | HIS3 | ADE2 | LacZ | HIS3 | ADE2 | LacZ |
| SML1 | + | – | 3.3 ± 0.1 | + | + | 31 ± 4 | + | – | NA | + | – | 4 ± 1 |
| RNR1 | + | + | 85 ± 1 | + | +/– | 2.9 ± 0.5 | – | – | NA | – | – | 0.8 ± 0.2 |
| RNR2 | – | – | 0.9 ± 0.4 | – | – | NA | + | +/– | 2.3 ± 0.4 | – | – | 1.4 ± 0.1 |
| vector | – | – | 0.4 ± 0.1 | – | – | NA | – | – | NA | – | – | NA |

For the HIS3 and ADE2 reporters, + signifies growth on histidine-less and adenine-less media. +/– signifies constructs unable to grow on adenine-less medium but able to give rise to white colonies on YPD medium (see Experimental Procedures).
LacZ activity was measured in Miller Units (Adams et al., 1997).
NA represents constructs that failed to give blue color on the filter assay and were not further tested.

TABLE 3

Yeast strains used in this study

| Strains | Genotype | Reference/Source |
|---|---|---|
| W1588-4C | MATa ade2-1 can1-100 his3-II,15 leu2-3,112 lrp1-1 ura3-1 | H. Zou and R. Rothstein |
| DLY258[a] | MATa mec1-1 sml1-1 bar1::hisG | T. Weinert |
| AMP107[b] | MATa HO::LYS2 ura3 trp1 lys2 leu2 | A. Mitchell |
| MCY3647[b] | MATα leu2-3,112 ura3-52 lys2-801 his3-Δ200 | M. Carlson |
| YCH13[b] | MATα his7 leu2 ade2 ade3 ura3 trp1 can1 sap3 | C. Hardy |
| U940 | MATa ade2Δ ade3Δ mec1-1 sml1-1(pRS416-ADE3-MEC1) | This Study |
| U946 | MATα ade2Δ ade3Δ SML1:URA3:SML1 | This Study |
| U952-3B | MATa sml1Δ::H153 | This Study |
| U953 | MATa/α mec1Δ:TRP1/MEC1 sml1Δ::H153/SML1 | This Study |
| U959 | MATa/α rnd53Δ::H153/RAD53 | This Study |
| U953-61A | MATa mec1Δ::TRP1 sml1Δ::H153 | This Study |
| U960 | MATa/α rad53Δ::H153/RAD53 sml1-1/SML1 | This Study |
| U960-5C | MATa rad53Δ::H153 sml1-1 | This Study |
| W1744-2C[a,c] | MATa niec1-8 lys2Δ | This Study |
| W1745-11C[a,c] | MATa niec1-3 lys2Δ | This Study |
| W1907-4A | MATα tel1Δ::LlRA3 | This Study |
| U971 | MATα dun1Δ::LlRA3 | This Study |
| R920 | MATa nup1Δ::LlRA3 (pFL39 MIP1) rad5 | F. Foury |
| R921 | MATa nup1Δ::LlRA3 (pFL39 nup1-1) rad5 | F. Foury |
| PJ69-4A[b] | MATa trp1-901 leu2-3,112 ura3-52 his3-200 gnl4Δ gal80Δ LYS2::GAL1-H153 GAL2-ADE2 met2::GAL7-lacZ | P. James |

All strains are isogenic or congenic (more than 10 backcrosses) to W303 (Thomas and Rothstein, 1989) unless otherwise noted. All W303 derivatives, except indicated, are RAD5. For W303-related strains, only alleles that differ from W303 are listed.
[a]4th backcross to W303.
[b]not related to W303.
[c]Parental strains were kindly provided by Ted Weinert (Weinert et al., 1994)

TABLE 4

Primers Used in This Study

| Name | Sequence |
|---|---|
| primer A | CTTCCAACTAAGAGCATGC |
| primer C | GCGATATCTAGCTGTATC |
| SML1-HIS3 5' | CTTACGGTCTCACTAACCTCTCTTCAACTGCTCAATAATTTCCCGGGATCCGCTGCACGGTCCTG |
| SML1-HIS3 3' | GTATGAAAGGAACTTTAGAAGTCCATTTCCTCGACCTTACCCTGGGCCTCGTTCAGAATGACACG |
| dun1d 5' | AGTAAAGGGGCTTAACATACAGTAAAAAAGGCAATTATAGTGAAGAGTCACGACGTTGTAAAACG |
| dun1d 3' | AAAATCCAGATTCAAACAATGTTTTTGAAATAATGCTTCTCATGTAGGAAACAGCTATGACCATG |
| p416-GAL 5' | ACGACTCACTATAGGGCGAATTGGGTACCGGGCCCCCCCTCGAGGTCGACGGCCCTTTCGTCTTCAAG |
| MEC1-GAL 3' | TCTTTTATTGCCAATATCAATTCGTCAAGATATTTGACGTGTGATTCCATGGATCCGGGGTTTTTCTC |
| pB-SML1 5' | GGGGATCCGGATGCAAAATTCCCAAGACTAC |
| pB-SML1 3' | GGGGATCCAAGGGAAAGGAAAATGCACG |
| pGBD-SML1 3' | AACTGCAGAAGGGAAAGGAAAATGCACG |
| RNR1-ORF 5' | GGGGATCCTCATGTACGTTTATAAAAGAGAC |
| RNR1 3' | AACTGCAGTTAGCTTGGCATTAGAATGG |
| RNR2 3' | AACTGCAGTTTTCCGATGCCCTTTCCAC |

TABLE 4-continued

Primers Used in This Study

| Name | Sequence |
| --- | --- |
| RNR2-ORF 5' | GGGGATCCTTACCATGCCTAAAGAGACC |
| RNR1-ORF 5' + 0 | GGGGATCCATGTACGTTTATAAAAGAGAC |
| RNR1 3' far | GCGTGTCGACGGCCTTCTTACAAGGACAG |
| pYX-SML1 5' | GGGGATCCTATGCAAAATTCCCAAGAC |
| HA 5' | GGGAATTCATGCGCATCTTTACCCATAC |
| HA 3' | GGGAATTCGCACTGAGCAGCGTAATC |

What is claimed is:

1. A screening assay for identifying a compound that is capable of reducing the division rate of a cell which comprises:
   (a) contacting the cell with a compound, wherein the compound consists of a fragment of the Sml1 protein or a peptidomimetic of the Sml1 protein, determined to mimic the binding of Sml1 protein to the large subunit of ribonucleotide reductase (Rnr1), which Sml1 protein comprises amino acids having the amino acid sequence set forth in SEQ ID NO: 2, and
   (b) comparing the division rate of the cell in step (a) with the division rate of the cell in the absence of the compound so as to determine whether the compound reduces the division rate of the cell, thereby identifying a compound capable of reducing the division rate of the cell.

2. The screening assay of claim 1, wherein the fragment is from about 20 amino acids to about 90 amino acids in length.

3. The screening assay of claim 1, wherein the cell is a yeast cell, a mammalian cell, a plant cell, an insect cell or a microbe.

4. The screening assay of claim 3, wherein the mammalian cell is a human cell, a hamster cell, a mouse cell, a rat cell or a monkey cell.

* * * * *

SEQUENCE LISTING

<160> NUMBER OF SEQ ID NOS: 27

<210> SEQ ID NO 1
<211> LENGTH: 1158
<212> TYPE: DNA
<213> ORGANISM: S. Cerevisiae

<400> SEQUENCE: 1

```
aatgagcaac cgtgtcaaca agagtgtcaa gaccggctac ttattcccca aggatcacgt      60
tccttctgcc aacatcattg ccgtcgaacg tcgcggcggt ctttctgaca ttggtaagaa     120
tacttccaac taagagcatg cttctctttt tttttgtagg ccaatgatag gaaagaacaa     180
tagattataa atacgtcaga atatagtaga tatgttttta tgtttagacc tcgtacatag     240
gaataattga cgttttttt tggccaacat ttgaaatttt tttttgttac ctcgcgctga      300
gcccaaacgg gctccactac ccgccgcggt cgccattttg ggaagtcatc cgtcccaaaa     360
aggaaatagc cataacatat cgttactgtt ttggaacatc gcccgtttcg cccgattccg     420
cctcagcggg tataaaaaga gatctttttt tttcctggct gtcccttcca tttttaaatg     480
tcttatctgc tcctttgtga tcttacggtc tcactaacct ctcttcaact gctcaataat     540
ttcccgctat gcaaaattcc caagactact tttacgctca aaatcgctgc caacaacaac     600
aagccccttc cacattgcgt accgtgacca tggcggaatt tagaagggtg cctttgccac     660
ctatggctga ggttcctatg ttgtctactc aaaactccat gggcagctcc gcttctgcct     720
ccgcttcttc attagaaatg tgggaaaagg atttggagga gagactcaac tctatcgatc     780
atgacatgaa caacaacaaa tttggttctg gcgaactaaa atctatgttc aaccagggta     840
aggtcgagga aatggacttc taaagttcct ttcatactct tttctttct ctttccattt      900
cccactagtt ctgttctttt cttctcttag ataccttctc tttcagggac tctcgtccta     960
ctattgttgt cattctcgaa acattctctc ccgtgcattt tcctttccct ttatatacat    1020
atatatatat atatatatat atgtctcttc tacgtatttt tgtatttctg tgtctttatc    1080
aaagatagtc tataatacgt ttgatacagc tagatatcgc tagcgccaac attgtccccc    1140
tctcttgatc aatgcttt                                                  1158
```

<210> SEQ ID NO 2
<211> LENGTH: 104
<212> TYPE: PRT
<213> ORGANISM: S. Cerevisiae

<400> SEQUENCE: 2

Met Gln Asn Ser Gln Asp Tyr Phe Tyr Ala Gln Asn Arg Cys Gln Gln

```
              1               5                  10                 15
            Gln Gln Ala Pro Ser Thr Leu Arg Thr Val Thr Met Ala Glu Phe Arg
                            20                  25                  30

Arg Val Pro Leu Pro Pro Met Ala Glu Val Pro Met Leu Ser Thr Gln
                            35                  40                  45

Asn Ser Met Gly Ser Ser Ala Ser Ala Ser Ser Leu Glu Met
                            50              55              60

Trp Glu Lys Asp Leu Glu Arg Leu Asn Ser Ile Asp His Asp Met
             65              70                  75                  80

Asn Asn Asn Lys Phe Gly Ser Gly Glu Leu Lys Ser Met Phe Asn Gln
                            85              90                  95

Gly Lys Val Glu Glu Met Asp Phe
                          100
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
cttccaacta agagcatgc                                               19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
gcgatatcta gctgtatc                                                18

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 5
cttacggtct cactaacctc tcttcaactg ctcaataatt tcccgggatc cgctgcacgg   60
tcctg                                                              65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 6
gtatgaaagg aactttagaa gtccatttcc tcgaccttac cctgggcctc gttcagaatg   60
acacg                                                              65

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 7 agtaaaggggg cttaacatac agtaaaaaag gcaattatag tgaagagtca cgacgttgta    60
aaacg    65

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: Primer

<400> SEQUENCE: 8
aaaatccaga ttcaaacaat gttttttgaaa taatgcttct catgtaggaa acagctatga    60
ccatg    65

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 9
acgactcact atagggcgaa ttgggtaccg ggccccccct cgaggtcgac ggccctttcg    60
tcttcaag    68

<210> SEQ ID NO 10
<211> LENGTH: 69
<212> TYPE: DNA
<213> ORGANISM: Artificial Sequence
<220> FEATURE:
<223> OTHER INFORMATION: Description of Artificial Sequence: Primer

<400> SEQUENCE: 10
tcttttattg ccaatatcaa ttcgtcaaga tatttgacgt gtgattccat ggatccgggg    60
tttttttctc    69

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11
ggggatccgg atgcaaaatt cccaagacta c    31

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
ggggatccaa gggaaaggaa aatgcacg    28

<210> SEQ ID NO 13
<211> LENGTH: 28
<212> TYPE: DNA
<213> ORGANISM: Artificial Sequence
<220> FEATURE:

```
<223> OTHER INFORMATION: Description of Artificial Sequence:  Primer

<400> SEQUENCE: 13
aactgcagaa gggaaaggaa aatgcacg                                28

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:  Primer

<400> SEQUENCE: 14
ggggatcctc atgtacgttt ataaaagaga c                           31

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:  Primer

<400> SEQUENCE: 15
aactgcagtt agcttggcat tagaatgg                               28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:  Primer

<400> SEQUENCE: 16
aactgcagtt ttccgatgcc ctttccac                               28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:  Primer

<400> SEQUENCE: 17
ggggatcctt accatgccta aagagacc                               28

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:  Primer

<400> SEQUENCE: 18
ggggatccat gtacgtttat aaaagagac                              29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:  Primer

<400> SEQUENCE: 19
gcgtgtcgac ggccttctta caaggacag                              29
```

```
<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:  Primer

<400> SEQUENCE: 20
ggggatccta tgcaaaattc ccaagac                                        27

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:  Primer

<400> SEQUENCE: 21
gggaattcat gcgcatcttt tacccatac                                      29

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:  Primer

<400> SEQUENCE: 22
gggaattcgc actgagcagc gtaatc                                         26

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:  PCR
      Oligonucleotide

<400> SEQUENCE: 23
caataatttc cccatatgca aaattcc                                        27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:  PCR
      Oligonucleotide

<400> SEQUENCE: 24
aaaggatcct tagaagtcca tttcctcgac                                     30

<210> SEQ ID NO 25
<211> LENGTH: 9
<212> TYPE: PRT
<213> ORGANISM: Peptide

<400> SEQUENCE: 25

Gly Ala Phe Thr Phe Asn Glu Asp Phe
1               5

<210> SEQ ID NO 26
<211> LENGTH: 9
<212> TYPE: PRT
<213> ORGANISM: Peptide

<400> SEQUENCE: 26
```

```
Lys Glu Ile Asn Phe Asp Asp Asp Phe
1               5
```

<210> SEQ ID NO 27
<211> LENGTH: 9
<212> TYPE: PRT
<213> ORGANISM: Peptide

<400> SEQUENCE: 27

```
Gln Gly Lys Val Glu Glu Met Asp Phe
1               5
```